United States Patent
Mault et al.

(10) Patent No.: US 6,629,934 B2
(45) Date of Patent: Oct. 7, 2003

(54) INDIRECT CALORIMETER FOR MEDICAL APPLICATIONS

(75) Inventors: James R. Mault, Evergreen, CO (US); Edwin M. Pearce, Jr., San Francisco, CA (US)

(73) Assignee: Healthetech, Inc., Golden, CO (US)

( * ) Notice: Subject to any disclaimer, the term of this patent is extended or adjusted under 35 U.S.C. 154(b) by 18 days.

(21) Appl. No.: 09/773,797

(22) Filed: Feb. 1, 2001

(65) Prior Publication Data

US 2001/0029340 A1 Oct. 11, 2001

Related U.S. Application Data

(63) Continuation-in-part of application No. 09/630,398, filed on Aug. 2, 2000.
(60) Provisional application No. 60/179,906, filed on Feb. 2, 2000, provisional application No. 60/179,961, filed on Feb. 3, 2000, provisional application No. 60/210,034, filed on Jun. 7, 2000, provisional application No. 60/228,388, filed on Aug. 28, 2000, and provisional application No. 60/236,829, filed on Sep. 29, 2000.

(51) Int. Cl.$^7$ ................................. A61B 5/08
(52) U.S. Cl. .............. 600/538; 600/529; 600/531; 600/532; 128/204.18; 128/204.21; 128/204.23; 128/204.26
(58) Field of Search ................. 600/300–301, 600/529, 531, 532, 538; 604/65–67; 128/202.15, 204.23, 205.23, 204.21, 204.22, 204.18, 204.26; 73/23.3

(56) References Cited

U.S. PATENT DOCUMENTS

| | | |
|---|---|---|
| 2,630,798 A | 3/1953 | White et al. |
| 2,826,912 A | 3/1958 | Kritz .................. 73/861.27 |
| 2,831,348 A | 4/1958 | Kritz .................. 73/861.28 |
| 2,838,399 A | 6/1958 | Vogel, Jr. |
| 2,869,357 A | 11/1959 | Kritz .................. 73/32 R |

(List continued on next page.)

FOREIGN PATENT DOCUMENTS

| | | |
|---|---|---|
| DE | 198 10 476 | 9/1998 |
| EP | 0459647 A2 | 2/1991 |
| EP | 0 712 638 | 12/1995 |
| GB | 2323292 | 9/1998 |
| WO | WO 96/40340 | 12/1996 |

*Primary Examiner*—Max F. Hindenburg
*Assistant Examiner*—Patricia Mallari
(74) *Attorney, Agent, or Firm*—Gifford, Krass, Groh, Sprinkle, Anderson & Citkowski, P.C.

(57) ABSTRACT

An improved respiratory analyzer comprises a disposable flow module and non-disposable electronics module. An improved ventilator system comprises a supply of respiratory gases, a ventilator line for directing the respiratory gases to a patient, a flow module holder located in series with the ventilator line into which a flow module can be inserted, and an electronics module which connects to the flow module. In a preferred embodiment, the flow module and electronics module operate in combination to provide the functionality of an indirect calorimeter, so as to determine the metabolic rate of the patient. Feeding of an intubated patient can be controlled using determined patient metabolic rates. Other respiratory parameters can be determined by the system, such as peak flow, tidal volume, end-tidal concentrations, and respiratory quotient. The system provides a non-invasive method of cardiac output determination. A flow module can also be inserted into the mouth or internal respiratory tube of a person.

36 Claims, 22 Drawing Sheets

U.S. PATENT DOCUMENTS

| | | | | |
|---|---|---|---|---|
| 2,911,825 | A | 11/1959 | Kritz | 73/861.03 |
| 2,920,012 | A | 1/1960 | Sanders et al. | |
| 3,213,684 | A | 10/1965 | Seaton et al. | |
| 3,220,255 | A | 11/1965 | Scranton et al. | 73/204.18 |
| 3,250,270 | A | 5/1966 | Bloom | |
| 3,306,283 | A | 2/1967 | Arp | |
| 3,523,529 | A | 8/1970 | Kissen | |
| 3,527,205 | A | 9/1970 | Jones | |
| 3,681,197 | A | 8/1972 | Smith | |
| 3,726,270 | A | 4/1973 | Griffis et al. | |
| 3,799,149 | A | 3/1974 | Rummel et al. | 600/531 |
| 3,814,091 | A | 6/1974 | Henkin | 128/202.22 |
| 3,834,375 | A | 9/1974 | Sanctuary et al. | 600/532 |
| 3,895,630 | A | 7/1975 | Bachman | 600/531 |
| 3,938,551 | A | 2/1976 | Henkin | 137/613 |
| 3,962,917 | A | 6/1976 | Terada | 600/537 |
| 3,979,480 | A | 9/1976 | Williams | |
| 4,003,396 | A | 1/1977 | Fleischmann | |
| 4,051,847 | A | 10/1977 | Henkin | 128/202.22 |
| 4,078,554 | A | 3/1978 | Lemaitre et al. | 600/539 |
| 4,186,735 | A | 2/1980 | Henneman et al. | |
| 4,188,946 | A | 2/1980 | Watson et al. | 128/204.22 |
| 4,197,857 | A | 4/1980 | Osborn | 600/531 |
| 4,200,094 | A | 4/1980 | Gedeon et al. | |
| 4,211,239 | A | 7/1980 | Raemer et al. | 600/531 |
| 4,221,224 | A | 9/1980 | Clark | |
| 4,230,108 | A | 10/1980 | Young | 128/207.15 |
| 4,233,842 | A | 11/1980 | Raemer et al. | 73/861.04 |
| 4,341,867 | A | 7/1982 | Johansen | 435/189 |
| 4,359,057 | A | 11/1982 | Manzella | |
| 4,363,238 | A * | 12/1982 | Willam | 73/204.21 |
| 4,368,740 | A | 1/1983 | Binder | |
| 4,386,604 | A | 6/1983 | Hershey | |
| 4,425,805 | A | 1/1984 | Ogura et al. | 73/861.29 |
| 4,440,177 | A | 4/1984 | Anderson et al. | 600/532 |
| 4,444,201 | A | 4/1984 | Itoh | |
| 4,463,764 | A | 8/1984 | Anderson et al. | 600/532 |
| 4,509,359 | A | 4/1985 | Gedeon et al. | 73/23.3 |
| 4,572,208 | A | 2/1986 | Cutler et al. | |
| 4,598,700 | A | 7/1986 | Tamm | |
| 4,608,995 | A | 9/1986 | Linnarsson et al. | |
| 4,619,269 | A | 10/1986 | Cutler et al. | |
| 4,648,396 | A | 3/1987 | Raemer | 128/204.22 |
| 4,658,832 | A | 4/1987 | Brugnoli | 600/532 |
| 4,719,923 | A | 1/1988 | Hartwell et al. | 128/663 |
| 4,724,845 | A | 2/1988 | Callahan | 600/531 |
| 4,753,245 | A | 6/1988 | Gedeon | |
| 4,756,670 | A | 7/1988 | Arai | 417/43 |
| 4,781,184 | A | 11/1988 | Fife | 128/205.12 |
| 4,796,639 | A | 1/1989 | Snow et al. | 600/532 |
| 4,832,042 | A | 5/1989 | Poppendiek et al. | 600/543 |
| 4,850,371 | A | 7/1989 | Broadhurst et al. | 600/532 |
| 4,856,531 | A | 8/1989 | Merilainen | 600/532 |
| 4,909,259 | A | 3/1990 | Tehrani | 600/531 |
| 4,914,959 | A | 4/1990 | Mylvaganam et al. | 73/861.28 |
| 4,917,108 | A | 4/1990 | Mault | |
| 4,955,946 | A | 9/1990 | Mount et al. | 600/532 |
| 4,986,268 | A | 1/1991 | Tehrani | 128/204.22 |
| 4,998,018 | A | 3/1991 | Kurahashi et al. | 250/343 |
| 5,022,406 | A | 6/1991 | Tomlinson | |
| 5,038,773 | A | 8/1991 | Norlien et al. | 128/205.23 |
| 5,038,792 | A | 8/1991 | Mault | |
| 5,042,500 | A | 8/1991 | Norlien et al. | 600/532 |
| 5,042,501 | A | 8/1991 | Kenny et al. | 600/532 |
| 5,060,506 | A | 10/1991 | Douglas | 73/24.01 |
| 5,060,655 | A | 10/1991 | Rudolph | 600/529 |
| 5,060,656 | A | 10/1991 | Howard | |
| 5,069,220 | A * | 12/1991 | Casparie et al. | 600/532 |
| 5,072,737 | A | 12/1991 | Goulding | |
| 5,081,871 | A | 1/1992 | Glaser | 73/863.23 |
| 5,095,900 | A | 3/1992 | Fertig et al. | 128/207.14 |
| 5,095,913 | A | 3/1992 | Yelderman et al. | |
| 5,103,814 | A | 4/1992 | Maher | 128/204.18 |
| 5,107,830 | A | 4/1992 | Younes | 128/204.18 |
| 5,117,674 | A | 6/1992 | Howard | 73/31.07 |
| 5,119,825 | A | 6/1992 | Huhn | 600/529 |
| 5,178,155 | A | 1/1993 | Mault | |
| 5,179,958 | A | 1/1993 | Mault | |
| 5,214,966 | A | 6/1993 | Delsing | 73/861.28 |
| 5,233,194 | A | 8/1993 | Mauze et al. | 250/341.2 |
| 5,233,996 | A | 8/1993 | Coleman et al. | 600/529 |
| 5,282,473 | A | 2/1994 | Braig et al. | 600/532 |
| 5,285,794 | A | 2/1994 | Lynch | |
| 5,293,875 | A | 3/1994 | Stone | |
| 5,299,579 | A | 4/1994 | Gedeon et al. | 600/532 |
| 5,303,712 | A | 4/1994 | Van Duren | 600/529 |
| 5,309,921 | A | 5/1994 | Kisner et al. | 600/532 |
| 5,326,973 | A | 7/1994 | Eckerbom et al. | 250/343 |
| 5,355,879 | A | 10/1994 | Brain | 128/207.15 |
| 5,357,972 | A | 10/1994 | Norlien | 600/538 |
| 5,363,857 | A | 11/1994 | Howard | 600/531 |
| 5,398,695 | A | 3/1995 | Anderson et al. | 600/532 |
| 5,401,966 | A | 3/1995 | Gray | 250/343 |
| 5,402,796 | A | 4/1995 | Packer et al. | |
| 5,419,326 | A | 5/1995 | Harnoncourt | 600/438 |
| 5,425,374 | A | 6/1995 | Ueda et al. | 600/532 |
| 5,450,193 | A | 9/1995 | Carlsen et al. | 356/301 |
| 5,468,961 | A | 11/1995 | Gradon et al. | 250/343 |
| 5,495,744 | A | 3/1996 | Ueda | 73/1.07 |
| 5,503,151 | A | 4/1996 | Harnoncourt et al. | 600/430 |
| 5,570,697 | A | 11/1996 | Walker et al. | 600/532 |
| 5,632,281 | A | 5/1997 | Rayburn | |
| 5,645,071 | A | 7/1997 | Harnoncourt et al. | 600/532 |
| 5,647,354 | A | 7/1997 | Lakhani et al. | 128/205.13 |
| 5,647,370 | A | 7/1997 | Harnoncourt | 600/538 |
| 5,676,132 | A | 10/1997 | Tillotson et al. | 128/204.23 |
| 5,705,735 | A * | 1/1998 | Acorn | 73/23.3 |
| 5,720,277 | A | 2/1998 | Olsson et al. | 128/204.22 |
| 5,754,288 | A | 5/1998 | Yamamoto et al. | 356/301 |
| 5,789,660 | A * | 8/1998 | Kofoed et al. | 73/23.2 |
| 5,796,009 | A | 8/1998 | Delsing | 73/861.28 |
| 5,800,360 | A | 9/1998 | Kisner et al. | 600/532 |
| 5,816,246 | A | 10/1998 | Mirza | 600/539 |
| 5,831,175 | A | 11/1998 | Fletcher-Haynes | 73/861.28 |
| 5,834,626 | A | 11/1998 | DeCastro et al. | 73/23.3 |
| 5,836,300 | A | 11/1998 | Mault | 128/204.23 |
| 5,839,901 | A | 11/1998 | Karkanen | 434/127 |
| 5,922,610 | A | 7/1999 | Alving et al. | 436/116 |
| 5,932,812 | A | 8/1999 | Delsing | 73/861.02 |
| 5,957,127 | A | 9/1999 | Yamamori et al. | 128/204.22 |
| 5,957,858 | A | 9/1999 | Micheels et al. | 600/529 |
| 6,010,459 | A | 1/2000 | Silkoff et al. | 600/532 |
| 6,044,843 | A | 4/2000 | O'Neil et al. | 128/204.23 |
| 6,058,786 | A * | 5/2000 | Wallen et al. | 73/861.28 |
| 6,099,481 | A | 8/2000 | Daniels et al. | 600/538 |
| 6,102,868 | A * | 8/2000 | Banner et al. | 600/484 |
| 6,131,571 | A * | 10/2000 | Lampotang et al. | 128/204.21 |
| 6,135,107 | A | 10/2000 | Mault | 128/204.23 |
| 6,139,506 | A * | 10/2000 | Heinonen | 600/532 |
| 6,206,837 | B1 | 3/2001 | Brugnoli | 600/529 |
| 6,345,538 | B1 * | 2/2002 | Kralbicher et al. | 73/861.27 |

* cited by examiner

INDIRECT CALORIMETER FOR MEDICAL APPLICATIONS

REFERENCED TO RELATED APPLICATIONS

This application is a continuation-in-part of U.S. patent application Ser. No. 09/630,398, filed Aug. 2, 2000, the contents of which are incorporated by reference. This application claims priority from U.S. provisional application Ser. Nos. 60/179,906, filed Feb. 2, 2000; 60/179,961, filed Feb. 3, 2000; 60/210,034, filed Jun. 7, 2000; 60/228,388, filed Aug. 28, 2000; and 60/236,829, filed Sep. 29, 2000, the contents of all of which are incorporated herein by reference.

FIELD OF THE INVENTION

This invention relates to the use of indirect calorimetry within health management, in particular for use with ventilators.

BACKGROUND OF THE INVENTION

In U.S. Pat. No. 5,989,188 Birkhoelzer et al. describe the use of an indirect calorimeter for determining the energy balance of a person. However, there is no description of how this would be achieved for a patient on a ventilator.

In U.S. Pat. No. 5,705,735, Acorn describes a method of determining nutritional requirements for a patient using an indirect calorimeter. However, the described system uses a pressure differential sensor to determine gas flow. The presence of a restriction in a flow tube can cause problems in medical applications. This system uses gas sampling for respiratory analysis, whereas the Applicant's invention uses analysis of gases in the flow path, providing an effectively instantaneous analysis of gas composition.

In U.S. Pat. No. 5,647,370 Harnoncourt describes an ultrasonic spirometer. In this application, the transducers are at an oblique angle to the flow tube axis. In U.S. Pat. No. 5,645,071 Harnoncourt et al. describe a method for determining the molar mass of a gas mixture using an ultrasonic method. In U.S. Pat. No. 5,503,151, Harnoncourt et al. describe the use of ultrasonic transducers in analyzing respiratory gases. The use of these spirometers in a mechanical ventilator system is not described.

In U.S. Pat. No. 5,179,958, Mault describes an indirect calorimeter from which the respiratory quotient and resting metabolic rate can be determined. However, this device is not optimized for use with an intubated patient. The use of a carbon dioxide scrubber adds weight and volume to a respiratory analyzer.

In U.S. Pat. No. 5,285,794, Lynch describes a respiratory gas monitor; however this device uses a gas mixing chamber and does not provide real time measurements of flow rates and gas component concentrations.

Other patents describing the use of oxygen and carbon dioxide sensors for metabolic monitoring include U.S. Pat. No. 5,072,737 to Goulding; U.S. Pat. No. 5,069,220 to Casparie et al.; U.S. Pat. No. 5,060,656 to Howard; U.S. Pat. No. 4,856,531 to Merilainen; U.S. Pat. Nos. 4,619,269 and 4,572,208 both to Cutler; and U.S. Pat. No. 4,233,842 to Raemer et al.

U.S. Pat. Nos. 4,917,108; 5,038,792; 5,178,155; 5,179,958; and 5,836,300, all to Mault, a co-inventor of the present application, are incorporated herein by reference. These patents disclose systems for measuring metabolism and related respiratory parameters through indirect calorimetry. These instruments generally employ flow meters which pass both the inhalations and the exhalations of a user breathing through the instrument and integrate the resulting instantaneous flow signals to determine total full flow volumes. In some embodiments, the exhaled gases generated by the user are passed through a carbon dioxide scrubber before passing through the flow meter so that the differences between the inhaled and exhaled volumes is essentially a measurement of the oxygen consumed by the lungs. In other embodiments, the concentration of carbon dioxide exhaled by the user is determined by passing the exhaled volume through a capnometer and integrating that signal with the exhaled flow volume. The oxygen consumption can then be calculated as the difference between the inhaled and exhaled oxygen volumes, corrected to standard conditions.

Recently, James R. Mault, M. D. and others invented an improved indirect calorimeter, more fully described in U.S. application Ser. No. 09/630,398, the contents of which are incorporated herein by reference. The improved calorimeter comprises an ultrasonic detection apparatus combined with a fluorescence oxygen sensor. This improved calorimeter can be adapted for use with an intubated patient, or other patient connected in some manner to a mechanical ventilator or respirator.

The oxygen consumption of a person is related to their resting metabolic rate (RMR). This can increase up to several hundred percent in certain trauma victims, such as burn patients. In addition, the nutritional requirements of a person are also determined by their metabolic rate. An enhanced RMR can lead to muscle wasting of a patient, as muscle burning proceeds in order to supply the person with the required additional energy. Hence, for optimized recovery of a patient, it would be valuable to know their nutritional requirements.

In addition, the correct ventilation of a patient requires knowledge of carbon dioxide and oxygen levels in the blood. The carbon dioxide and oxygen levels in arterial blood can be determined using the end tidal gas component concentrations of exhaled breath.

SUMMARY OF THE INVENTION

The present invention provides an improved respiratory analyzer for use in a ventilator system, or other system to assist with breathing. An improved ventilator system for a patient comprises a ventilator unit providing respiratory gases, a tube (or line or conduit) for conveying respiratory gases to the patient, a flow module holder located within the tube (such as a slot, holder, clip, or the like); a flow module being be placed in the holder so that respiratory gases pass through a flow path of the flow module; and an electronics module, connected to the flow module and containing an electronic circuit having processor, designed to calculate a flow rate for respiratory gases flowing through the flow path. In a preferred embodiment, oxygen consumption volumes and metabolic rates are calculated by the electronics module.

It is an object of the present invention to provide an improved system by which the metabolic rate of an intubated patient can be determined.

It is a further object of the present invention to provide a system for improved respiratory control of a patient on a ventilator.

It is a object of the present invention to provide improved respiratory analysis for a patient on a ventilator or other means of respiratory assistance.

DETAILED DESCRIPTION OF THE INVENTION

Figure 1:
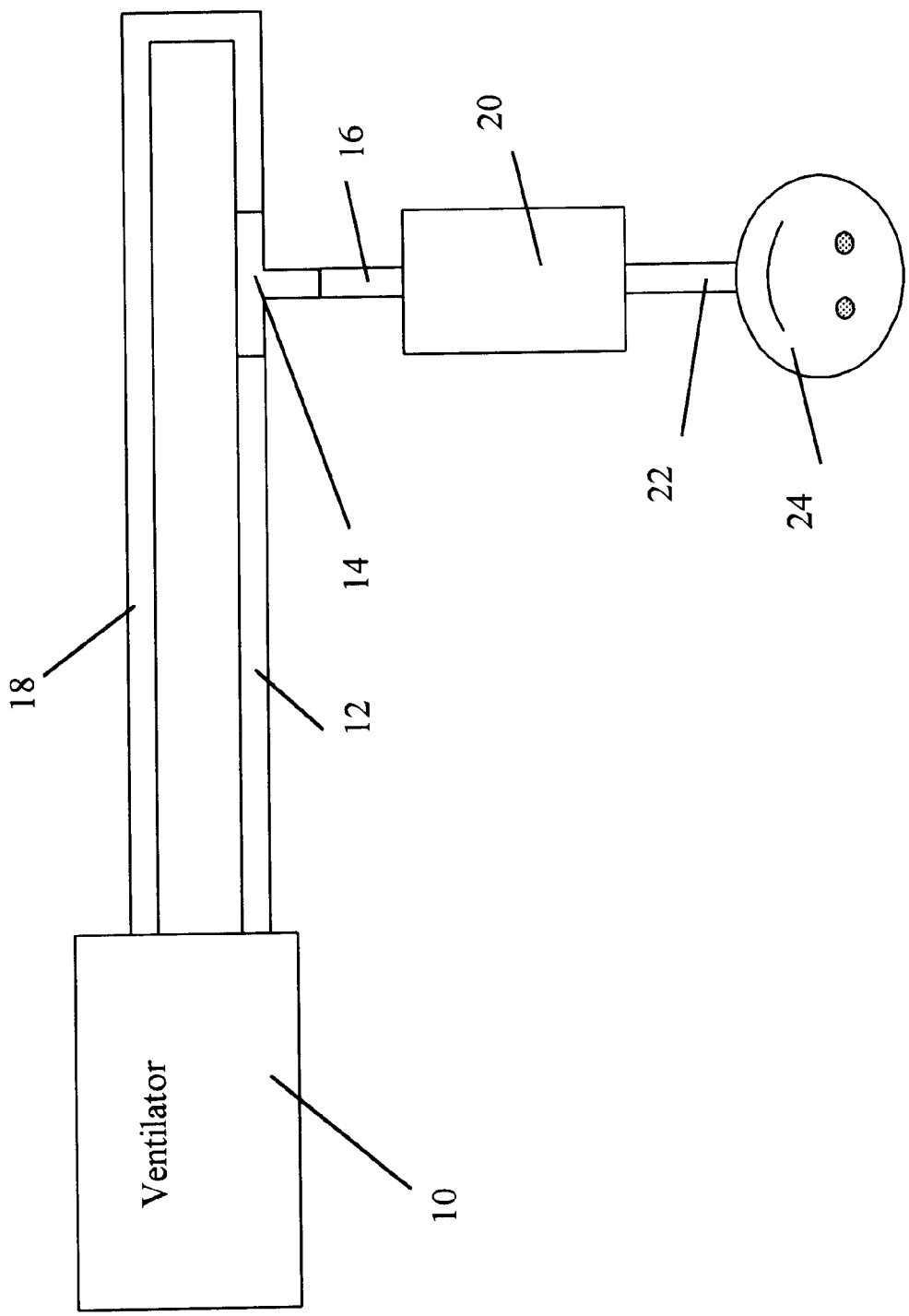
FIG. 1 shows a general schematic of a ventilator system.

FIG. 1 shows a ventilator system. The system comprises a ventilator 10, an inlet tube 12, a valve unit 14, a valve connector 16, a return tube 18, a respiratory analyzer 20, and a patient intubation device 22 connecting to patient 24. In a conventional respirator system, the respiratory analyzer 20 may be the pneumotach described by Acorn in U.S. Pat. No. 5,705,735. In embodiments of the present invention, the improved indirect calorimeter described in U.S. application Ser. No. 09/630,398 is adapted for use as an improved respiratory analyzer in a ventilator systems, such as the system shown in FIG. 1. However, the present invention can be adapted for other ventilator systems known in the art.

Referring to FIG. 1, ventilator 10 provides a source of inhalation gas during inhalation of the patient, which passes through the inlet tube 12 to the valve 14. The valve 14 allows the inhalation gas to pass through to the valve connector 16, and so through the respiratory analyzer 20 and the intubation device 22 to the patient 24. The intubation device may be placed in the mouth of the patient, or into the trachea. During exhalation, exhaled gas passes out through the intubation device 22, respiratory analyzer 20, and valve connector 16 to the valve 14. The valve 14 allows the exhaled gas to pass through to the return tube 18, and so pass back to the ventilator unit 10. The valve unit is typically T-shaped or Y-shaped, and in part acts to prevent exhaled gases entering the inlet tube 12, to minimize rebreathing of exhaled carbon dioxide.

In preferred embodiments, the respiratory analyzer 20 is located close to the mouth of the patient, but outside of the patient's body. In other embodiments, described later, components of an improved respiratory analyzer may be located inside the body of the patient within a respiratory tube such as the trachea.

Referring again to FIG. 1, the inlet tube 12 forms an inlet conduit (or inhalation conduit) for directing inhalation gases to the patient. The connector 16 and intubation device 22 form a respiratory conduit, through which both inhaled and exhaled air flow. The flow module is preferably inserted into the respiratory conduit, so that both inhaled and exhaled gases pass through the flow module. The return tube 18 forms a return conduit (or exhalation conduit) for exhaled gases. The valve 14 allows inhaled gases to pass from the inhalation conduit to the respiratory conduit, and allows exhaled gases to pass from the respiratory conduit to the exhalation conduit. Exhaled gases may also be vented to the atmosphere. In the configuration of FIG. 1, respiratory gases pass in both directions through the flow module (inhaled gases and exhaled gases pass in opposite directions). The ventilator 10 serves as a supply of respiratory gases. For partial rebreathing and cardiac output studies, the valve may be configured to allow some gas to pass from the exhalation conduit back into the respiratory conduit, as discussed later in relation to cardiac output measurements.

Figure 2:
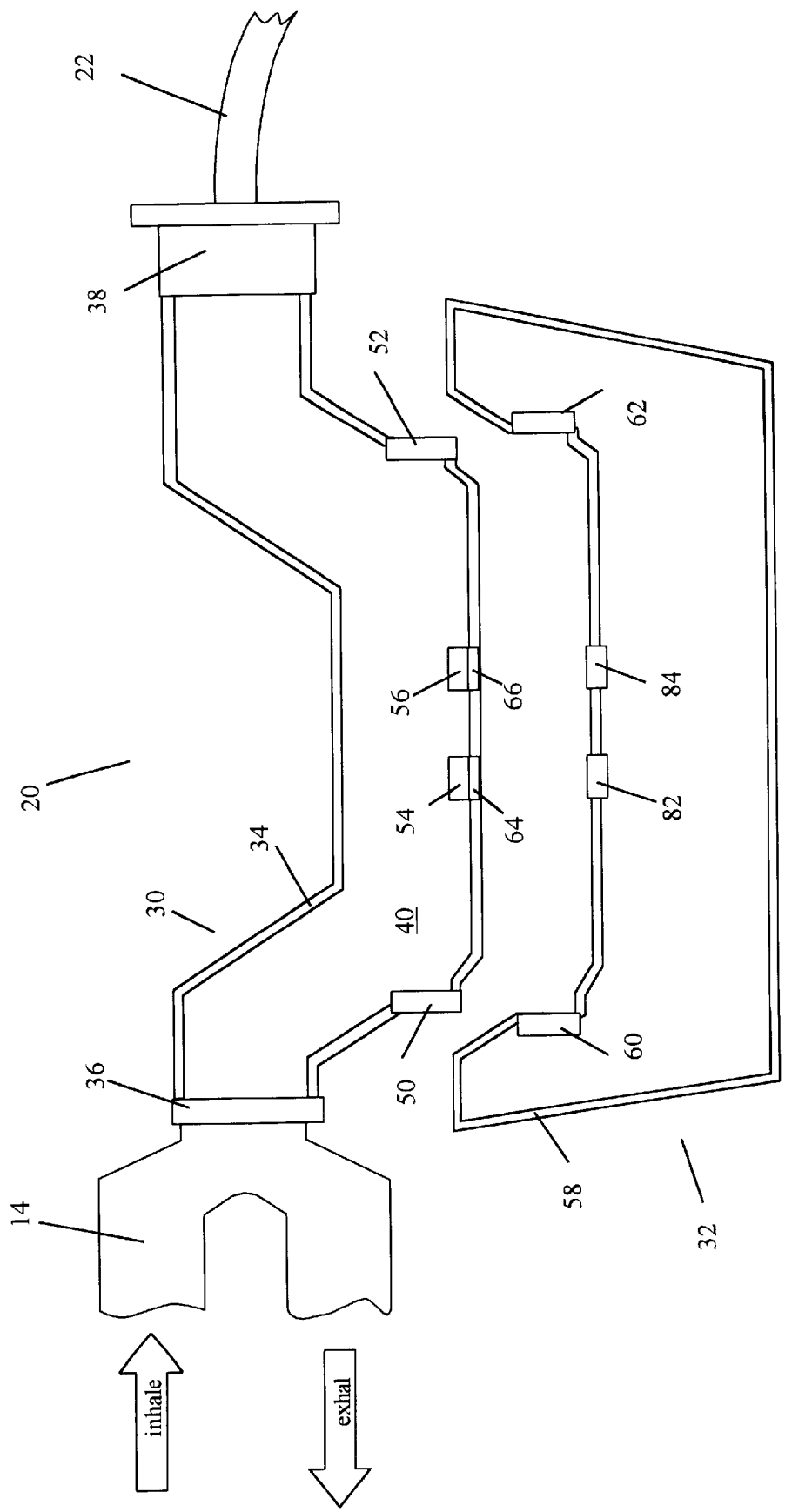
FIG. 2 shows a schematic of an improved respiratory analyzer.

FIG. 2 shows a cross-sectional view of an improved respiratory analyzer, shown generally at 20, and comprising two parts: a flow module 30, and an electronics module 32. The modules 30 and 32, shown in cross-section, are adapted to be attached to each other for analysis of respiratory gases flowing through the flow module, and to be detached from each other for sterilization or disposal of the flow module. In a preferred embodiment, the flow module 30 is a disposable part of the respiratory analyzer 20, whereas the electronics module 32 is a non-disposable part. FIG. 2 shows the flow module 30 connected between valve 14 and intubation device (or respiratory connector) 22 using connector 36 and collar 38. A valve connector may be added between the valve 14 and analyzer 20, for optimized placement of the flow module relative to the patient.

Flow module 30 has a housing 34 which encloses as flow path 40. Connector 36 and collar 38 provide fluid coupling between gases in the flow path 40 and gases in the valve 14 and intubation device 22. Respired gases pass through the flow module 30, which is changed if another patient is connected to the ventilator, and may be changed at intervals for the same intubated patient. The flow module has first and second ultrasonic transducers 50 and 52, an oxygen sensor film 54 and a carbon dioxide sensor film 56. Ultrasonic transducers 50 and 52 are mounted on the housing 34 so as to have ultrasonic coupling with gases flowing along the flow path 40, to provide a flow rate sensor. Gas sensor films 54 and 56 have elements in fluid communication with the flow path 40, so as to allow compositional analysis of gases flowing through the flow path 40. Embodiments of flow module are described more fully below. The electronics module shown generally at 32 forms a reusable portion of the respiratory analyzer. The module 32 comprises a housing 58, a first transducer interface 60. and a second transducer interface 62. The module 32 preferably contains the electronic circuitry required to measure and analyze flow rates and gas component compositions, as discussed in parent application Ser. No. 09/630,398 and in further detail below. The housing of module 32 is adapted to be removably mounted to module 30, using any convenient attachment, so that an electrical connection is formed between the transducers (50 and 52) and transducer interfaces (60 and 62). The attachment may comprise a clip, screw, magnetic strip, hook-and-loop attachment (Velcro). Preferably the housing of the two modules are formed so that the housing of module 32 snaps into a mechanical guide in the housing of 30 (or vice versa).

FIG. 2 shows the flow module to be supported between two sections of the respiratory gas conduit using the connector 36 and collar 38. The connector and collar hence form a flow module holder. The holder is in series with the respiratory line, so that gases passing along the line pass through a flow module placed within the holder. In other embodiments, the flow module holder may comprise a mechanical bridge connecting two sections of the respiratory conduit, such as the valve and the intubation device, having a slot or other mechanical structure into which the flow module is inserted so that the flow path of the flow module becomes part of the respiratory gas conduit. A locking mechanism may be provided to prevent the flow module from falling out of the holder. In other embodiments, the non-disposable electronics module is used to form a mechanical bridge between two sections, and the flow module is inserted so as to make electrical connection with the electronics module and fluid connection between the flow path and the sections of the respiratory conduit.

FIG. 2 also shows an oxygen sensor module 82 and carbon dioxide sensor module 84 mounted on the housing of the electronics module. When the electronics module is connected to the flow module, the sensor modules detect gas component concentration levels in the flow path of the flow module using fluorescent sensor films 54 and 56. Ports 64 and 66 allow interaction of the sensor modules and the fluorescent sensor films. In the preferred embodiment, the sensor modules contain a radiation source (such as a light emitting diode), reference photodetector, and a sensor photodetector. The ports are recesses having a transparent window. The radiation from the light emitting diode in the sensor module irradiates sensing and reference regions of the fluorescent film. Sensing regions produce fluorescent radiation with an intensity, frequency, or decay time correlated with gas component concentration. Reference regions are insulated from the effects of gas component concentration, for example using a gas-impervious film. The sensor and reference photodetectors detect radiation from sensing and reference regions of the fluorescent film, respectively. Analysis of the signals is fully described in the parent application, and gas sensor configurations discussed further below. In other embodiments, gas sensors are contained within the flow module. These may be extracted and sterilized for re-use when the flow module is disposed of.

In other embodiments, connections to transducers 50 and 52 may be brought to a single socket, and a corresponding plug provided on the electronics module. The modules may then be connected by a cable. In further embodiments, the ultrasonic transducers may be located in the electronics module, in place of transducer interfaces 60 and 62, and pathogen-resistant, ultrasound-transmitting windows used in the flow module in place of transducers 50 and 52.

Figure 3:
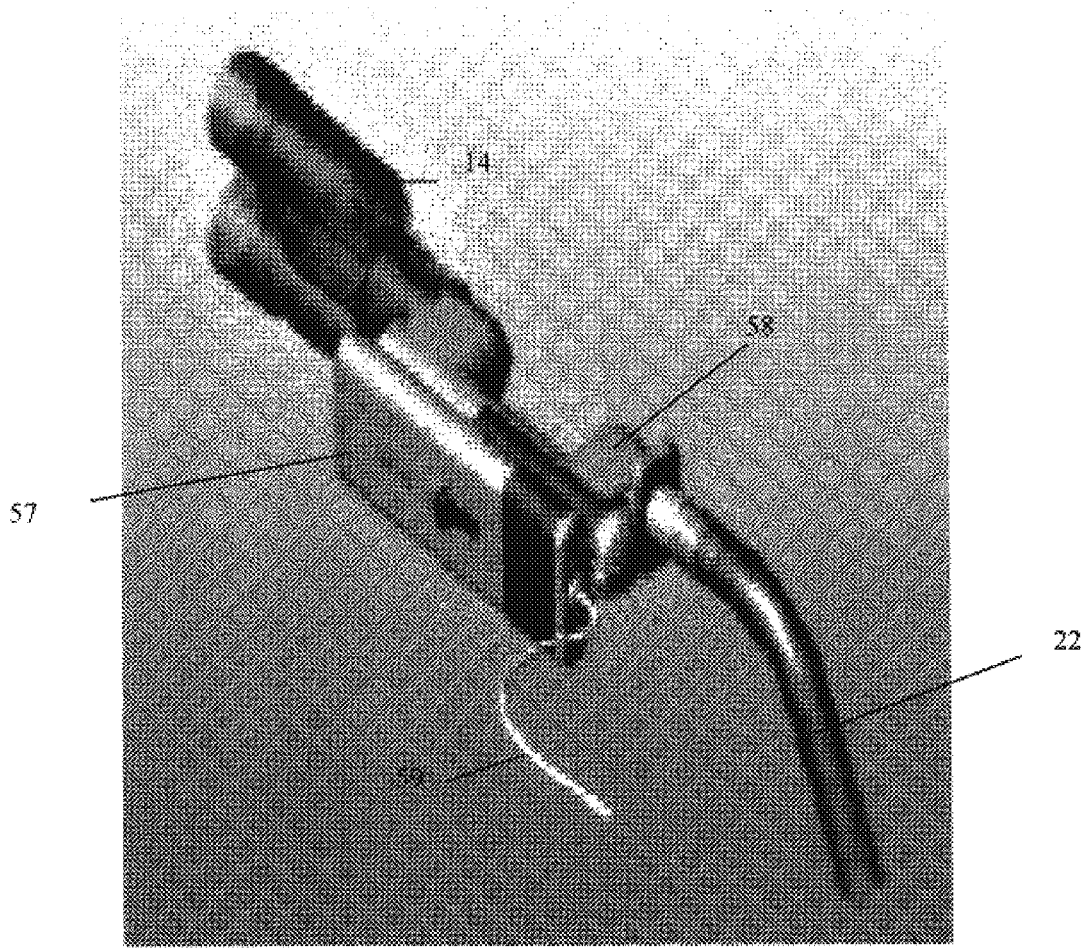
FIG. 3 shows a design for an improved respiratory analyzer.

FIG. 3 shows a design for an improved respiratory analyzer, in the form of a three-dimensional computer rendering. This perspective drawing shows a non-disposable section, incorporating the primary portions of the sensors and electronics, indicated at 57, having cable connector 59, supported by connection to the disposable section 58, which is in turn supported in the respirator line between the patient and a respirator pump.

Figure 4:
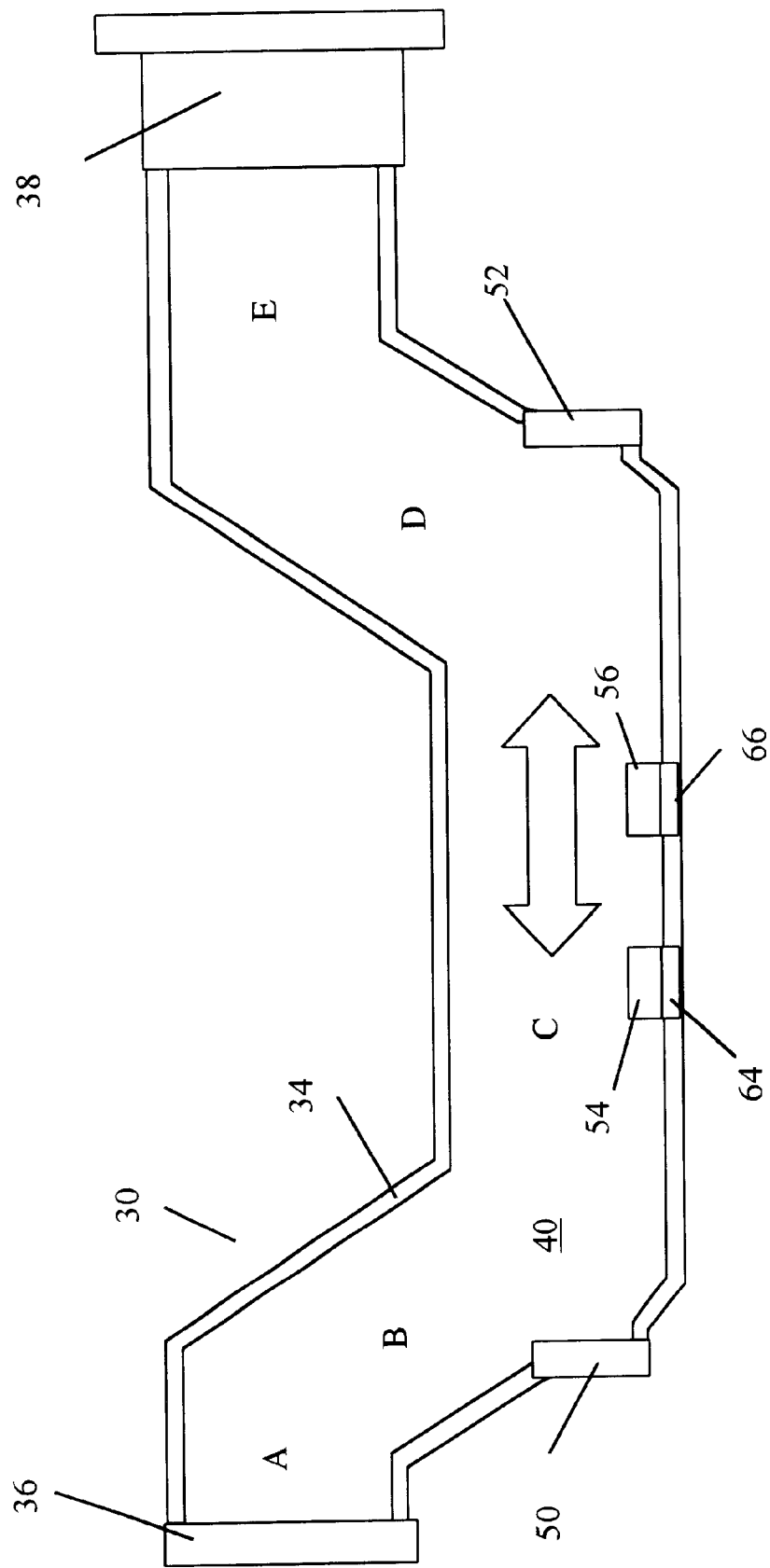
FIG. 4 shows a flow module embodiment.

FIG. 4 shows further details of the flow module embodiment shown at 30 FIG. 2. The housing 34 of flow module 30 encloses a flow path 40. The flow path has an inlet portion A, a first lateral offset portion B, a central portion C, a second lateral offset portion D, and an outlet portion E. The terms inlet and outlet portion relate to the direction of gas flow during inhalation. For convenience, we will discuss the flow path with reference to inhalation (the flow direction is reversed during exhalation).

The flow path 40 is not straight, having the flow path central portion C with a lateral spatial offset from a path which would directly link sections A and E, due to the presence of lateral offset (or oblique) flow sections B and D. The purpose of this design is to allow ultrasonic flow analysis of gases flowing along the central portion of the flow path C, using ultrasonic pulses communicated between transducers 50 and 52. In this configuration, the path of the ultrasonic pulses is directly along the flow path section C. This is an improvement over the configurations described by Harnoncourt in which ultrasonic pulse propagation is in a direction oblique to the gas flow direction, for example as shown in U.S. Pat. Nos. 5,503,151 and 5,645,071. If the pulse direction and gas flow directions are not parallel, angular corrections need to be applied to the ultrasonic data, and the sensitivity of the ultrasonic technique is reduced.

Gas sensor films 54 and 56 are disposed on the side of the flow path 40 so as to allow gas component concentrations to be determined. Preferably, the concentrations are determined at a point near midway between the ultrasonic transducers, to allow more accurate integration of component gas volumes from flow rates and gas concentration values. However, gas sensor films may be located elsewhere in the flow path if convenient. The sensor films will be discussed in more detail later.

The ultrasonic transducers are used to determine flow rates, and by integration with gas component concentration measurements, flow volumes are determined, as described in U.S. application Ser. No. 09/630,398. The molar mass of inhaled and exhaled gases can be determined using ultrasonic pulse transit time measurements, as described more fully in International Pat. App. No. WO 00/7498 to Mault. Hence, gas concentration sensors can be omitted in some embodiments, for the purpose of lowering costs. Recently, low cost micro-machined ultrasonic transducers became available from suppliers such as Sensant, of San Leandro, Calif., as described in International Pat. App. Nos. WO 00/11730 and WO 00/72631, herein incorporated by reference. Low-cost transducers are preferably used in the disposable flow module 30. Amplified or processed transducer signals may be transmitted to the electronics module.

Figure 5:
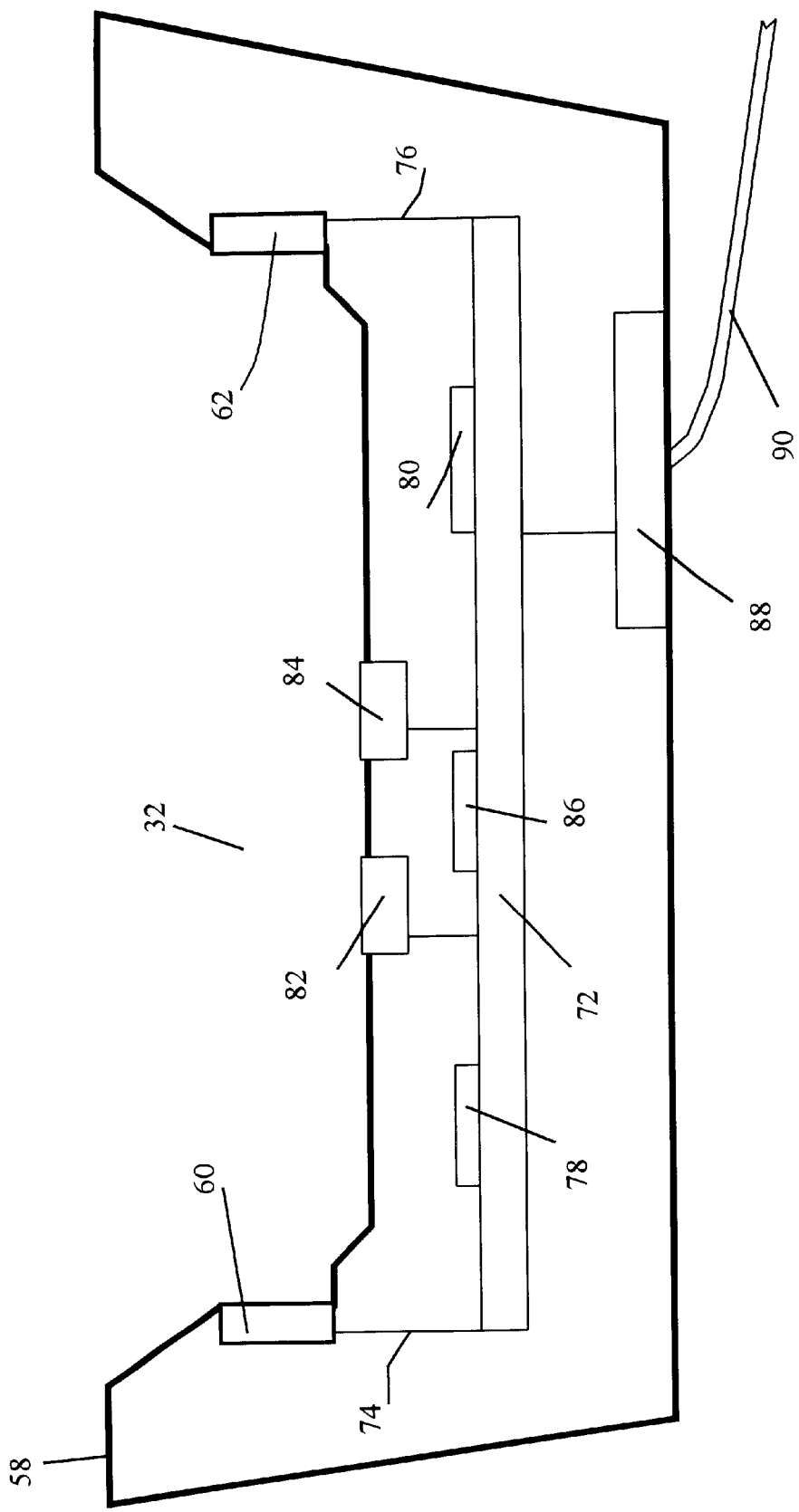
FIG. 5 shows an electronics module embodiment.

The electronics module shown generally at 32, best shown in FIG. 5, forms a reusable portion of the respiratory analyzer. The module 32 comprises a housing 58, a circuit board 72 disposed within the housing, a first transducer interface 60 and transducer connector 74 so as to allow communication with transducer 50 of the flow module, a second transducer interface 62 and connector 76 so as to allow communication with the transducer 52. Electronic circuitry is provided to determine gas flow from ultrasonic pulse transit data. The module 32 preferably contains the electronic circuitry required to measure and analyze flow rates and gas component compositions, including a processor 78, ASIC 80, and other circuitry adapted to process the signals from the sensors, such as a timer, memory, and display, for example as described in U.S. application Ser. No. 09/630,398. The electronics module also contains sensor film analyzers 82 and 84, and sensor analysis circuitry 86. The electronics module 32 processes the signals from the sensors and provides data on flow volumes and gas component concentrations. Data can be transmitted to another device using interface unit 88 and cable 90.

In other embodiments, the electronics module 32 can be a stand-alone unit, a unit which clips onto the flow tube, or may be integrated into the electronic circuitry of the ventilator 10, or integrated into other medical equipment in proximity to the patient. Circuitry to allow ultrasonic analysis of gas flow rates, suitable for inclusion in the electronics module, is described in U.S. Pat. No. 5,214,966 to Delsing, incorporated herein by reference. In other embodiments, a respiratory analyzer adapted to measure flow rates and carbon dioxide concentration of exhaled air may be located at any convenient point along the return tube (element 18 in FIG. 1), or inside the ventilator itself.

The electronics module receives data from ultrasonic flow sensors, gas analysis sensors, and any other sensors which may be included in the flow module, such as a humidity sensor, pressure sensor, and a temperature sensor. Micromachined ultrasonic transducers may be designed containing micromachined temperature, pressure, and humidity sensing elements. The processing of collected data is preferably as described in parent application Ser. No. 09/630,398.

Hence, when the flow module and electronics module are attached together, the electronics module receives signals from the ultrasonic transducers and gas sensors. The electronic circuitry needed to analyze these signals has been discussed in the parent application. The electronic circuit determines flow rates from the transit time of ultrasonic pulses along the flow path, between the two ultrasonic transducers. Gas concentrations are determined using the ratio of sensing to reference level fluorescence from the fluorescent films. Flow rates and gas concentrations are determined effectively on an instantaneous basis, i.e. on a time scale such as milliseconds which is much faster than that of breathing. In this context, real time measurements of flow and gas component concentrations are those made on an effectively instantaneous time scale. A processor within the electronics module then integrates the flow values with gas component concentration value so as to determined volumes of gases inhaled or exhaled. Breath direction, beginning, and end are determined as described in the parent application. More generally, the term instantaneous, in regard to flow or concentration sensing, refers to a time period much less (such as one tenth or less) than the time period over which a flow volume is to be calculated. Fluorescence gas component concentration sensors and ultrasonic flow sensors are effectively instantaneous with regard to respiratory analysis applications. Preferably, an in-line flow meter is used, which provides measures flow rates directly within the flow path, such as a pair of ultrasonic transducers.

The combination of flow module and electronics module forms the respiratory analyzer, and in the preferred embodiment the respiratory analyzer has the functionality of an indirect calorimeter, as described fully in the parent application. The combination of flow rate and oxygen concentration measurements in inhaled and exhaled breaths allows oxygen consumption to be measured, and hence metabolic rate to be determined. The respiratory quotient may be assumed, determined directly using a carbon dioxide sensor, determined using the methods of the parent application, or estimated from the nutritional balance of the food that the patient is receiving. The metabolic rate determined by the indirect calorimeter can be displayed on a display, such as a liquid crystal display, on the housing of the flow module, or transmitted to another electronic device, such as the ventilator or feeding device, for display. In other embodiments, a portable computing device adapted to receive data from the flow module, for example a PDA (personal digital assistant) provided with a data logging card, may be used as the electronics module.

In other embodiments, sensors and transducers within the flow module are connected to an interface module, such as a plug, socket, Bluetooth wireless transmitter, IR transmitter, or the like, which enables data to be transmitted to the electronics module.

In other embodiments, some or all of the sensor and transducer drive and detection circuitry are contained within the flow module. The electronics module preferably contains a processor for combining, correcting, and analyzing data, and an ASIC for analysis of ultrasound data. The flow module preferably contains a power supply, such as a battery or electrical power input, and power to sensors in the flow module is preferably supplied through the connection to the electronics module. The gas component sensors may contain analog to digital conversion circuitry, so as to provide a digital signal or concentration dependent frequency signal to the electronics module. In further embodiments, the flow module communicates with the electronics module using a wireless link. The flow module then will contain a power supply of its own, and circuitry sufficient to transmit data signals from the transducers and sensors to the electronics module.

In ventilator applications, it is preferable to locate the processing electronics away from the face of the person. This reduces the weight of the flow tube pressing on the person, and removes sources of heat away from the sensors, improving sensor accuracy. To achieve this, the flow module and electronics module may be connected by a cable connection, or a wireless communication link such as the Bluetooth protocol can be used.

Further embodiments of the flow module are now described below.

The coaxial flow geometry of preferred embodiments of the indirect calorimeter (Gas Exchange Monitor, or GEM) described in U.S. application Ser. No. 09/630,398 can be adapted for use in ventilator systems. The flow resistance should be low enough so as not to present problems for patients with respiratory problems, and so the diameter of the flow path may be increased in relation to that described in U.S. application Ser. No. 09/630,398. However, increasing the diameter of the flow path can reduce accuracy of the flow measurements and lead to increased dead space. From studies with the Gas Exchange Monitor (GEM) described in U.S. application Ser. No. 09/630,398, the coaxial geometry is known to give accurate results.

Figure 6A:
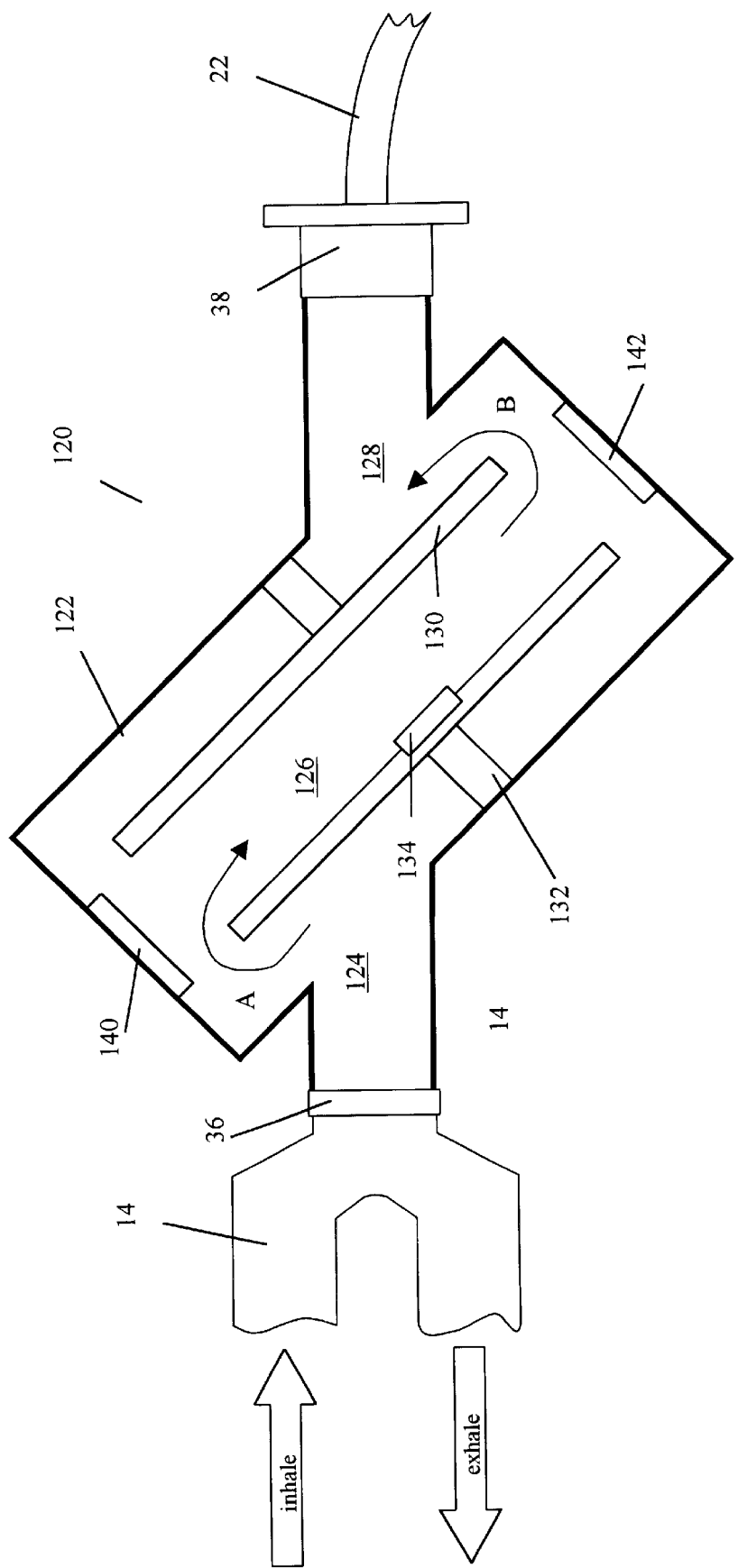
FIG. 6A shows a flow module embodiment having a coaxial flow geometry.

FIG. 6A shows another preferred embodiment of the flow module (shown in cross-section) having a coaxial flow geometry. The coaxial flow tube module shown generally at 120 has a housing 122, enclosing a flow path formed by first chamber 124, central flow path 126, and second chamber 128. A flow tube 130, generally circular in a preferred embodiment, surrounds the central flow path 126. The chambers 124 and 128 have toroidal portions surrounding the flow tube 130. Ultrasonic transducers 140 and 142 are mounted so as to communicate ultrasonic pulses along the flow path 126 formed by the flow tube 130. Chambers 124 and 128 are separated by partition 132.

In the case of inhaled air, inspired air enters chamber 124 from the valve 14, and passes into the chamber portion surrounding the flow tube 130. Inhaled air then enters central flow path 126, for example as indicated by arrow A. Air then passes through the central flow path 126, and then enters second chamber 128, for example as shown by arrow B. The ultrasonic transducers 140 and 142 are used to measure the flow rate along the central flow path 126. An oxygen sensor 134 measures the concentration of oxygen in the gas flowing through the main flow path. The oxygen sensor may be also located at other positions, such as in first chamber 124, or in second chamber 128.

Wires may connect the oxygen sensor and ultrasonic transducers to an interface connector, into which an electronics module, cable (for example leading to an electronics module), or wireless transmitter (for example communicating with an electronics module) may be plugged.

Figure 6B:
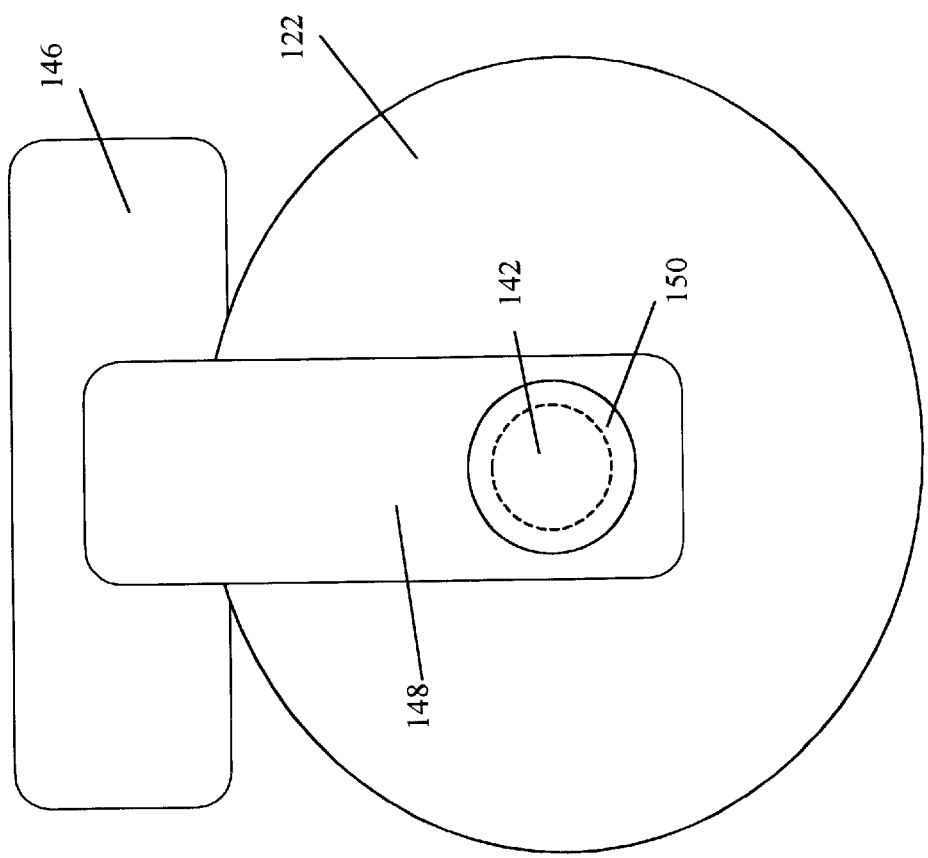
FIG. 6B shows a coaxial flow module docked to an electronics module.

FIG. 6B shows an end-view of a detachable electronics module attached to the housing 122 of the flow module. The electronics module has housing 146, with an extended portion 148 having an ultrasonic transducer interface 150, which forms a connection to ultrasonic transducer 142 of the flow module. At the other end of the flow module and electronics module, a similar connection is made between a transducer interface of the detachable electronics module and the ultrasonic transducer 140.

Figure 7:
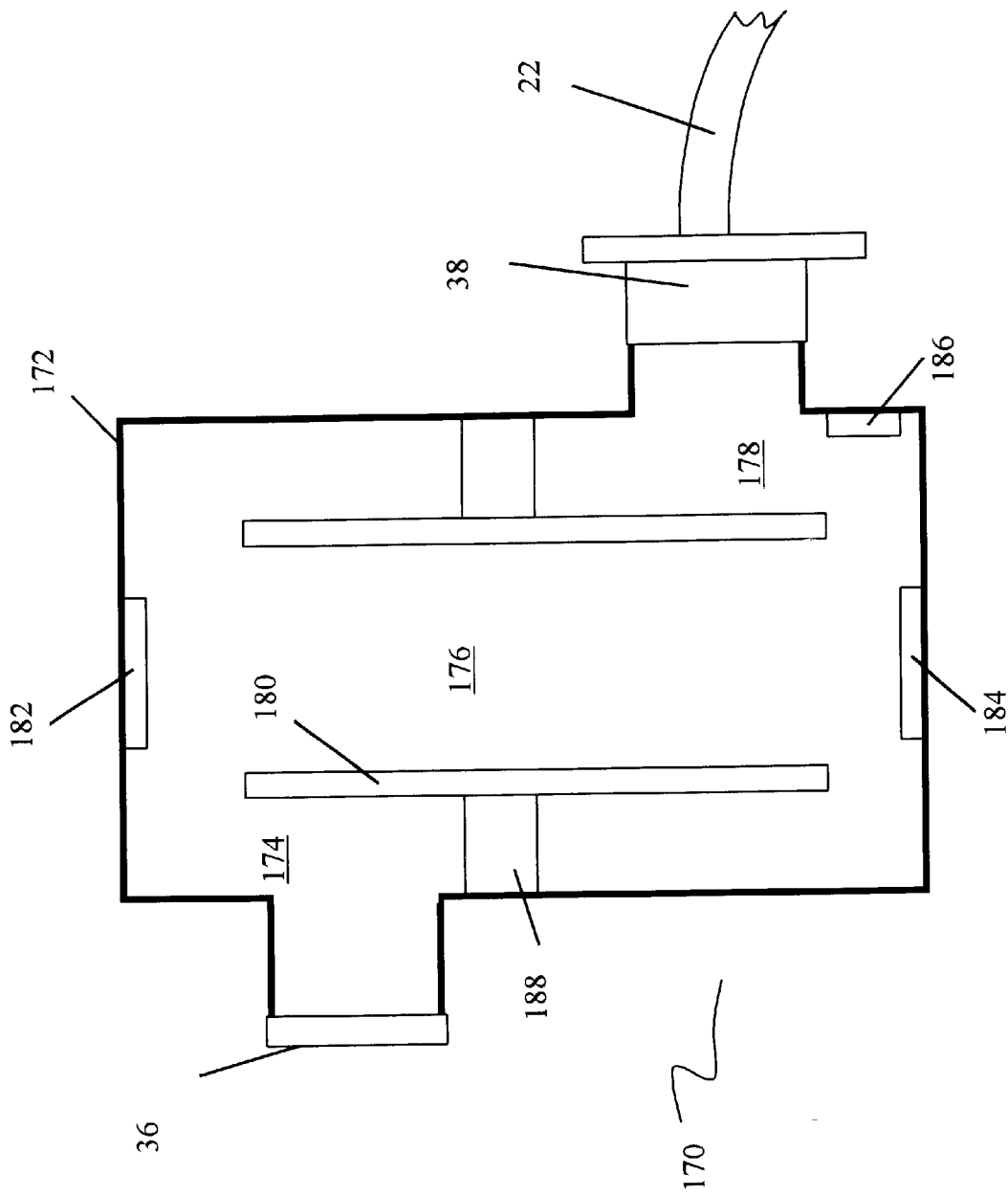
FIGS. 7 and 8 show further flow module embodiments having coaxial flow geometries.

FIG. 7 shows an embodiment of the flow module that is a slight modification from the design shown in FIG. 6. In this embodiment, the direction of the central flow path is substantially perpendicular to the flow direction of inhaled air path through connector 36 and collar 38.

The flow module embodiment, shown generally at 170, has a housing 172, enclosing a flow path formed by first chamber 174, central flow path 176, and second chamber 178. The central flow path is formed by flow tube 180, which is preferably generally circular. Ultrasonic transducers 182 and 184 are disposed so as to communicate via ultrasonic pulses propagating along central flow path 176. An oxygen sensor is provided in the second chamber 178 so as to measure instantaneous oxygen concentration in the gas flow through the flow module. A chamber separator 188 separates the first and second chambers 174 and 178.

Figure 8:
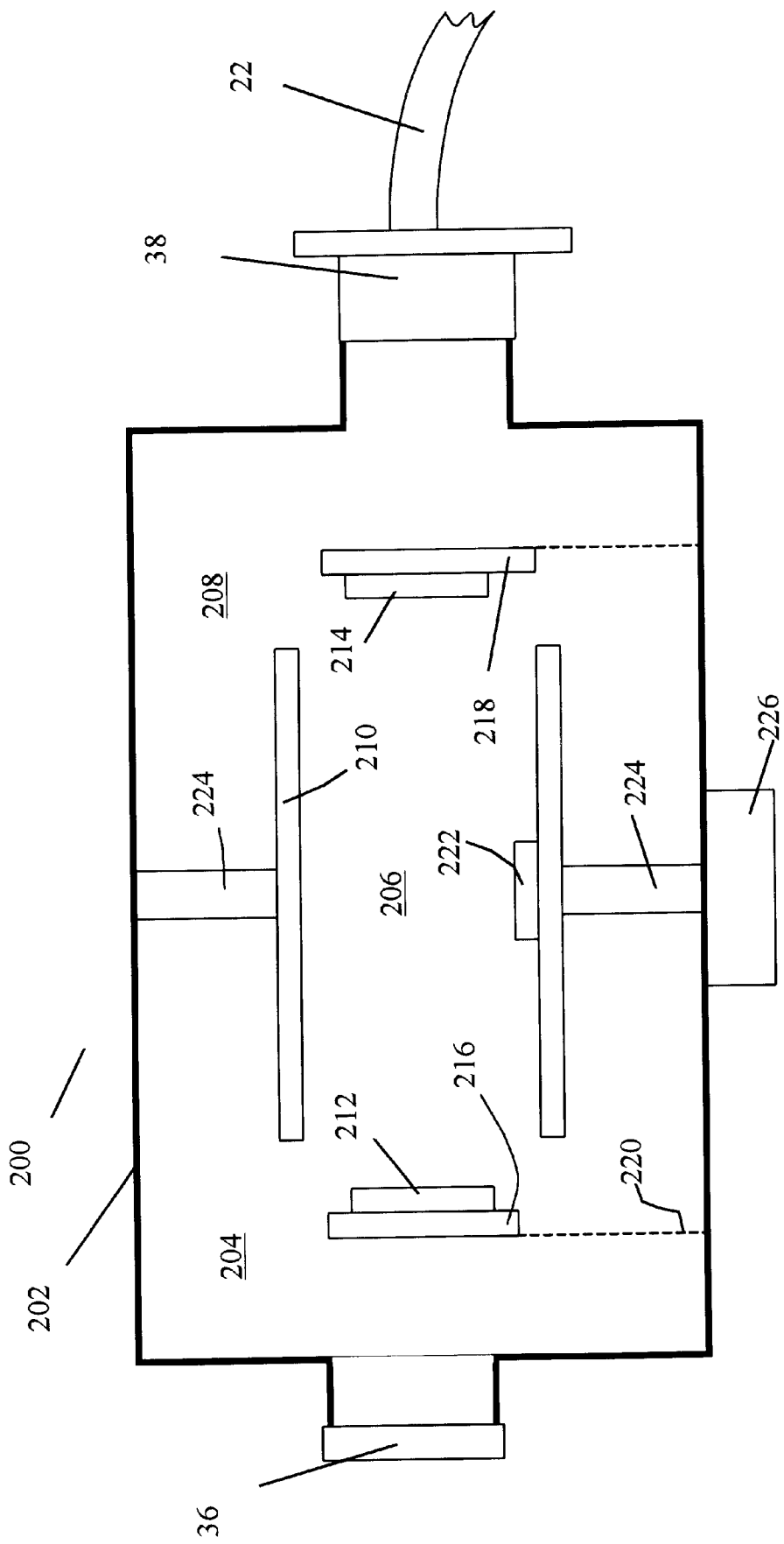

FIG. 8 shows a further embodiment of the flow module that is another modification of the design shown in FIG. 6. The flow module, shown in cross-section at 200, has housing 202 enclosing a ventilator-side chamber 204, a central flow path 206 formed by flow tube 210, and a patient-side chamber 208. Ultrasonic transducers 212 and 214 are located so as to measure the transmission times of ultrasonic pulses along the flow path 206. Transducer 212 is mounted on transducer support 216, and transducer 214 is mounted on transducer support 218. The transducer supports are supported, relative to the housing 202, by one or more struts 220, drawn as dotted lines as they may not be in the plane of the cross section. An oxygen sensor 222 is preferably located on the inside surface of the flow tube 210. Chamber separator 224 separates the two chambers 204 and 208, and supports flow tube 210 generally centrally within housing 200. An interface module 226 mounted on the housing 200, in the form of an electrical socket, allows connection to an electronics module.

Electrical connection to the ultrasonic transducers is made through one or more struts. Electrical or optical access to the oxygen sensor 222 is made through the chamber separator 224. The struts 220 do not substantially impede gas flow through the device, and do not divide up the chambers 204 and 208. The struts 220 are shown perpendicular to the long axis of the housing 200, but they can have any reasonable angle and point of attachment to the housing. In other embodiments, the oxygen sensor may be located on the inside surface of the housing 202 for easier electrical or optical access.

Other possible embodiments of the flow module will now be described.

Figure 9:
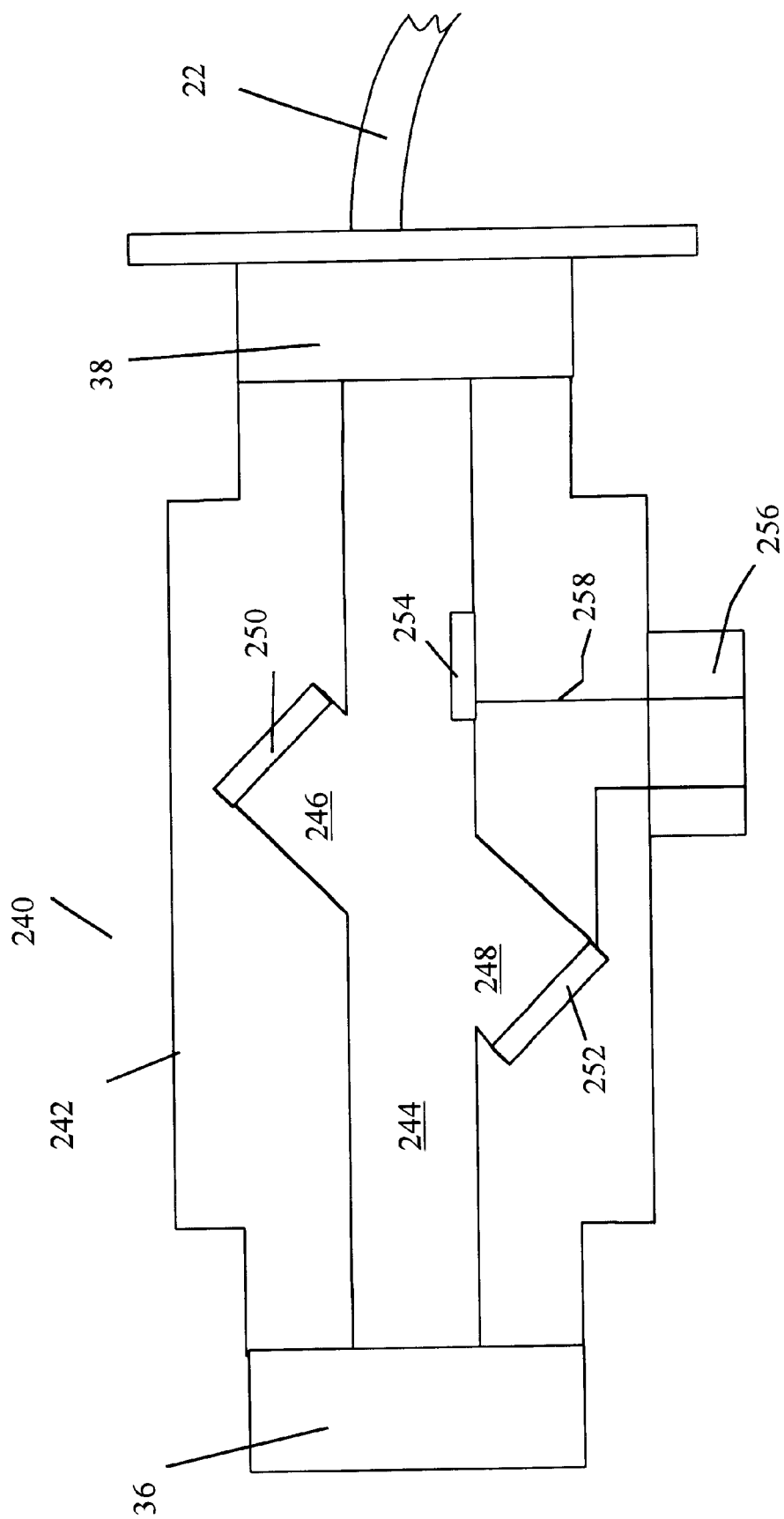
FIG. 9 shows a flow module having ultrasonic transducers in an oblique configuration.

FIG. 9 shows a flow module, shown generally at 240, having housing 242 surrounding a central flow path 244. Recesses 246 and 248 are formed within the inside surface of the housing, coupling ultrasonic transducers 250 and 252 with the central flow path. An oxygen sensor 254 is mounted so as to be exposed to a gas flow along the central flow path. The ultrasonic transducers and oxygen sensor are connected to an interface unit 256, using wires such as 258. The oxygen sensor may also be connected optically to the interface unit.

The ultrasonic transducers communicate along a path oblique to the flow path 204. The use of ultrasound to measure flow rates and volumes in such a configuration is described by Harnoncourt in U.S. Pat. Nos. 5,647,370, 5,645,071, 5,503,151, and 5,419,326, the contents of which are incorporated herein in their entirety by reference. The use of bacteria-resistant membranes with such transducers is described by Wallen et al. in U.S. Pat. No. 6,058,786, incorporated herein by reference.

In the preferred embodiment, the electronics module plugs into the flow module using the interface unit 256. In other embodiments, a cable can be connected to the flow module 240 so as to provide power to the transducers, and to allow data transfer between the flow module and the electronics module, which can be a free-standing unit. In other embodiments, the electronics module can be in wireless communication with the flow module. In this case, the flow module preferably contains an independent power source, such as a battery.

Figure 10:
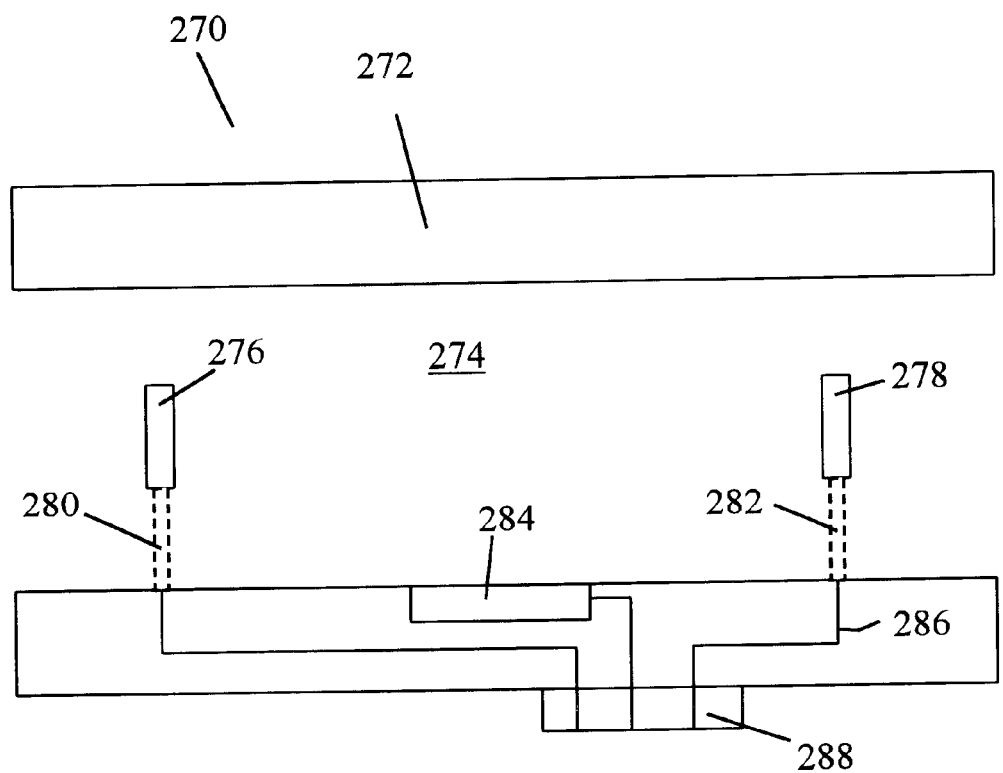
FIG. 10 shows a flow module having ultrasonic transducers in the flow.

FIG. 10 shows a flow module, shown generally at 270, having a housing 272 surrounding flow path 274. The housing is generally cylindrical. Ultrasonic transducers 276 and 278 are disposed directly within the flow path 274, and are each supported by one or more struts such as 280 and 282, designed to minimize flow path impedance. An oxygen sensor 284 is located on the inner surface of housing. Wires such as 286 connect the transducers and sensor to an interface unit 288, to which an electronics module or communications module can be connected.

Micromachined ultrasonic transducers may be sufficiently inexpensive to be used in a disposable flow module. A plurality of transducers may be supported at various positions in the flow path, so as to measure flow profiles and so determine more accurate flow volumes. In this case, the transducers are preferably small so as not to significantly disturb the flow profile. The flow distribution across the flow tube cross section can be modeled using conventional techniques, as a function of measured flow rate, and the model results used to improve the accuracy of the flow rate data. The interface unit 288 forms an electrical interface between the transducers, sensor and external devices. A cable can connect to an electronics module.

In preferred embodiments, the flow module contains one or more a gas sensors, so as to determine concentration of gases passing through the flow path of the flow module. For metabolic rate measurements, one or more gas sensors sensitive to oxygen or carbon dioxide are preferably used. However, oxygen consumption (or carbon dioxide production) can be determined from ultrasound measurements alone, as discussed in International Pat. App. No. WO 00/7498 to Mault, the contents of which are included herein by reference.

In preferred embodiments, the gas sensor used is (or are) fluorescence sensors, such as described by Colvin and others in U.S. Pat. Nos. 5,917,605, 5,910,661, 5,894,351, and 5,517,313, the contents of which are herein incorporated by reference, and World Pat. Appl. Nos. WO98/52024, WO98/52023, WO99/46600, and WO00/13003, the contents of which are incorporated herein by reference. However, other sensors can be used. For example, a laser based sensor can be used, for example as described in U.S. Pat. Nos. 5,570,697 and 6,091,504, incorporated herein by reference. Other sensor technologies may be used, including Raman scattering based sensors, IR absorption or emission based sensors, zirconia detectors such as described in U.S. Pat. No. 4,995,256, photoacoustic sensors, and micromachined sensors.

Figure 11:
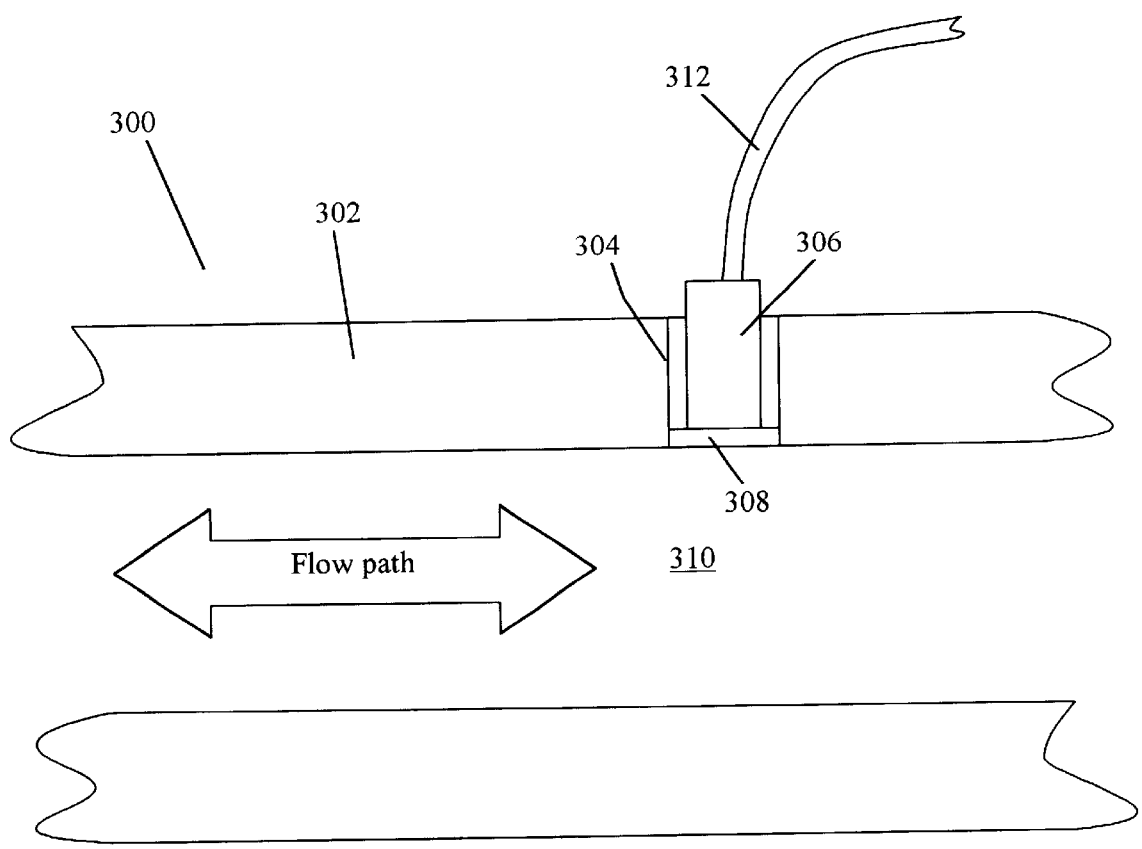
FIG. 11 shows a flow module adapted to receive an oxygen sensor.

FIG. 11 shows a partial cross-section of a flow module adapted to receive an external oxygen sensor. The flow module 300 has a generally cylindrical body 302 having an indentation 304 in the top surface (as shown) adapted to receive an oxygen sensor 306. The oxygen sensor is separated from the flow path 310 by oxygen permeable membrane 308. The oxygen sensor responds effectively instantaneously to oxygen concentration changes in the flow path 310. In this context, instantaneous refers to time scale much shorter than that of a breath, such as on a millisecond scale. A cable 312 is used to convey data from the sensor to an electronic processing module. Preferably, the oxygen sensor can be removed from the flow module, allowing disposal or sterilization of the flow module.

Figure 12:
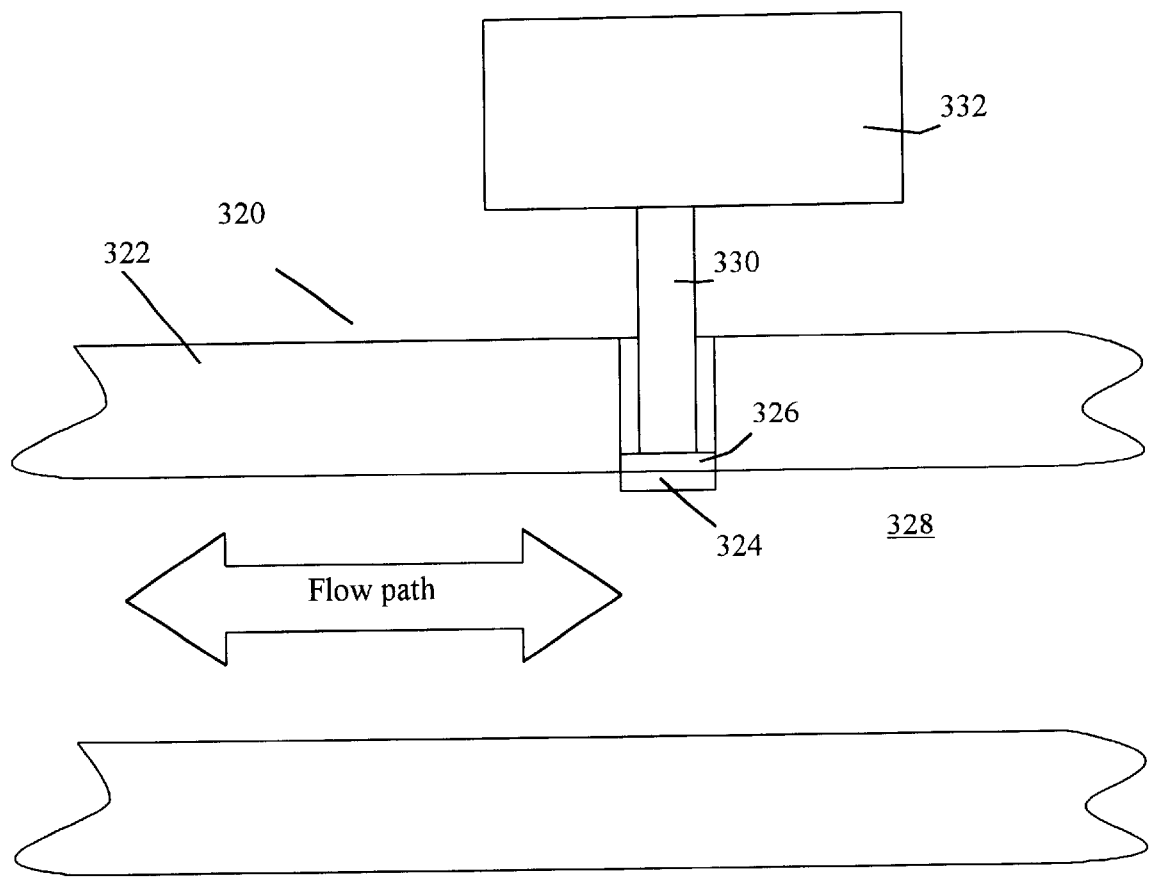
FIG. 12 shows a flow module adapted to receive an optical fiber for oxygen sensing.

FIG. 12 shows a portion of a flow module 320 having a housing 322 and an oxygen sensitive fluorescent coating 324 on the inner surface of housing 322. A transparent membrane 326 separates the fluorescent element 324 from an external radiation source and detector. In this example, an optical fiber 330 used to convey excitation radiation to the fluorescent coating, and fluorescent radiation from the coating returns along the fiber. An electronics module 332 contains an excitation radiation source and fluorescent radiation detector. The electronics module can be detachably mounted to the housing of the flow module, or may be at some distance away using a longer fiber. The housing of the flow module may be transparent, which would allow optical coupling to fluorescent films, and viewing of any colorimetric detectors of diagnostic respiratory components. In this example, removal of the fiber allows disposal of the flow module. The fluorescent chemistry may also be included in a film at the end of the fiber, or within the end of the fiber. In this case the fiber would fit through a hole in the housing 322 so as to expose the oxygen-sensitive chemistry to the flow path 328, and the fiber would be removed and disposed of between patients.

Figure 13:
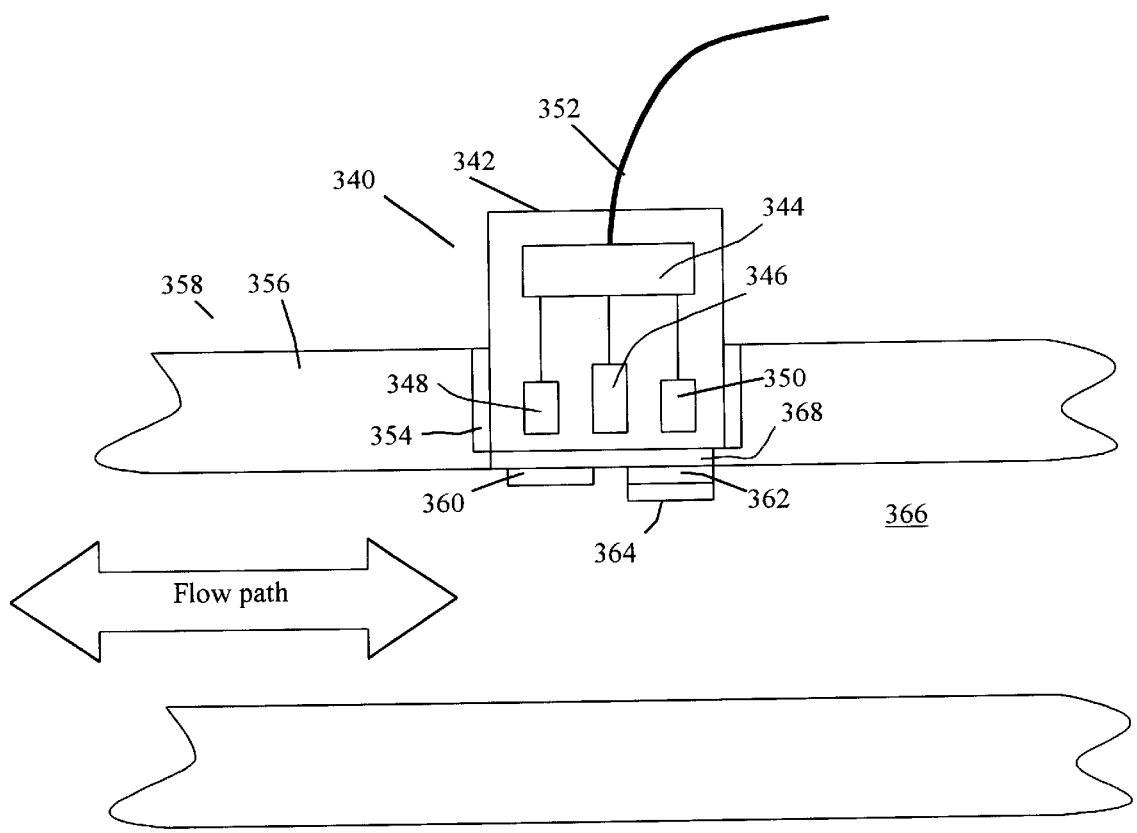
FIG. 13 shows an oxygen sensor with a fluorescent coating in contact with the flow path.

FIG. 13 illustrates an oxygen sensor analysis module 340, having a housing 342, electronics circuit 344, an excitation radiation source 346, a sensing channel optical detector 348, a reference channel optical detector 350, and external connection 352. The oxygen sensor analysis module is shown placed into an indentation 354 in the housing 356 (shown in part) of a flow module 358. The inner surface of the housing 356 has sensing channel fluorescent film 360 and reference channel fluorescent film 362 disposed on its inner surface. The surface of the sensing channel film 360 is exposed to respiratory gases passing through the flow path 366, whereas the reference channel film 362 is protected against the influence of oxygen by oxygen-impermeable film 364. A transparent waveguide film 368 allows optical coupling between the oxygen sensor analysis module and the fluorescent films. Preferably, the oxygen sensors in the flow module contain electronic circuitry so as to provide a signal correlated with oxygen content in the gas flow. Determination of oxygen concentration, including the application of calibration factors, is preferably achieved using the electronics module. The oxygen detector may comprise an analog to digital converter, so as to provide a digital signal to the electronics module.

The oxygen sensor analysis module can be separated from the fluorescent elements disposed on the inner surface of the tube body. The object of this configuration is to allow reuse of the electronic part of the oxygen sensor, while allowing the fluorescent element to be disposed along with the flow tube. The module may be removed before sterilization or disposal of the flow module. This has the advantage of allowing a lower cost disposable element, which is an important aspect of reducing the cost of the inventive ventilator system.

The excitation radiation source 346 is preferably a blue light emitting diode, and optical detectors (photodetectors) 348 and 350 are located so as to receive fluorescent radiation from oxygen sensitive fluorescent element 360 and oxygen insensitive fluorescent element 362, respectively. The cable 352 allows connection to an external electronics module, possibly using the interface module of previous embodiments. The electronic circuitry necessary for analysis of fluorescence oxygen sensor signals is described in parent application Ser. No. 09/630,398.

In other embodiments, an oxygen sensor may be a unitary device, comprising the analysis module, transparent film, and fluorescent films, which reversibly pushes into a hole through the wall of the flow tube. The fluorescent films may be periodically replaced if they degrade over time.

The oxygen sensor is preferably combined with an ultrasonic flow module for measurement of oxygen consumption by the patient. Other flow determination methods may be used, such as flow meters based on the cooling rate of an element, and flow meters based on pressure drops across an obstruction (such as described by Rodder in U.S. Pat. No. 5,313,955, incorporated by reference).

In other embodiments, a carbon dioxide detector may be present, in addition to or instead of the oxygen detector. The carbon dioxide sensor preferably uses a chemical with a fast response charge in carbon dioxide concentration. Carbon dioxide sensor technologies include fluorescent films, IR detection, Raman detection, and other spectroscopic techniques. Micro-mechanical sensors may be used, in which the frequency of an oscillation is modified by surface absorbed carbon dioxide.

There are advantages to including gas sensors sensitive to other gases. For example, nitric oxide is sometimes administered to a patient to improve breathing. The use of nitric oxide sensors, coupled with flow measurements, allows the volume of nitric oxide gas administered to the patient to be determined. Exhaled gas contains gas components which may be usefully detected as diagnostic of the patient condition. For example, exhaled nitric oxide can indicate airway inflammation. In this case, a qualitative nitric oxide indication, for example colorimetric, may be used. The housing of the flow module may be transparent, or contain a window, so as to allow a colorimetric sensor to be observed. It is also advantageous to detect exhalation components indicative of abnormal metabolism. For example, ketones (such as acetone), aldehydes (such as acetaldehyde), and acid components (such as acetoacetic acid and 3-hydroxybutyric acid) can be indicative of low or unavailable blood sugar. In this case, administration of feeding or insulin may be urgently required. Ammonia in exhaled breath can be indicative of liver failure, as discussed in U.S. Pat. No. 5,425,374 to Ueda, incorporated herein by reference. The flow module of the present invention can be combined with other devices, such as those using sampling methods, to analyze respiratory components. These and other gas detecting methods are further described in co-pending U.S. provisional application No. 60/228,388 (filed Aug. 28, 2000), incorporated herein by reference.

Figure 14:
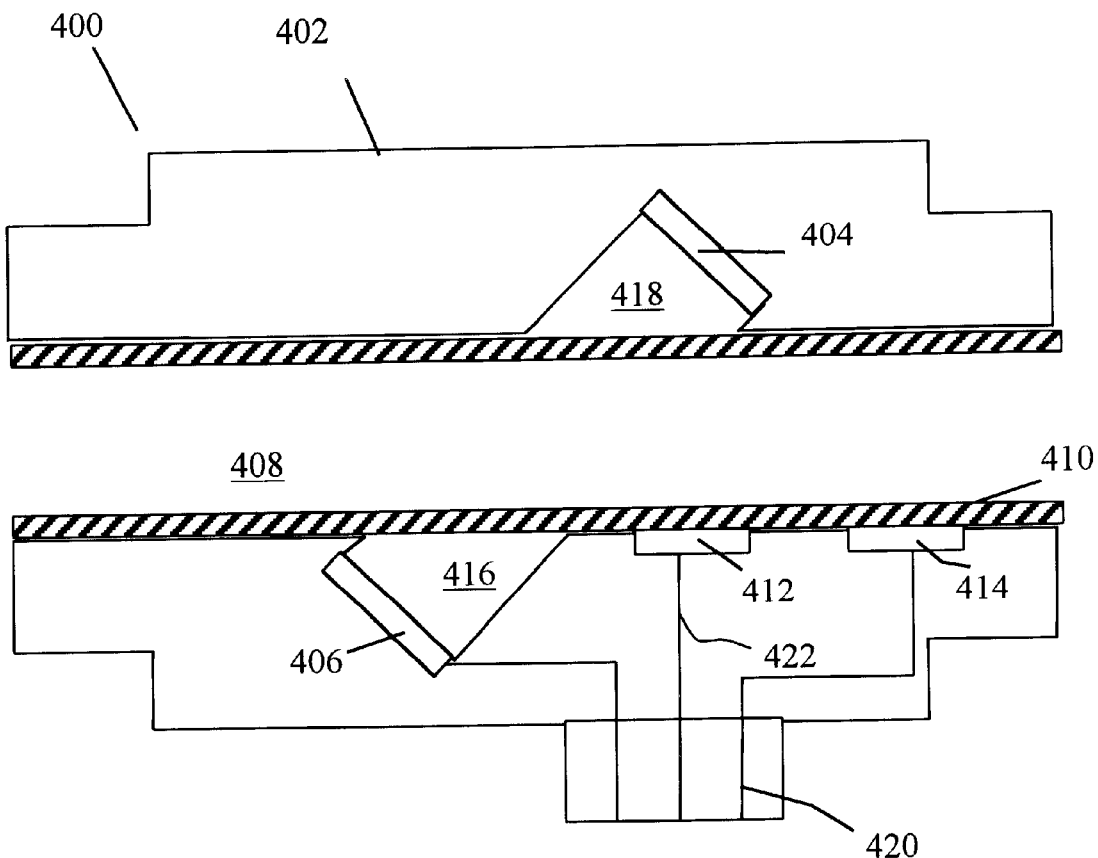
FIG. 14 shows a pathogen resistant liner for a flow tube.

FIG. 14 shows a flow module in cross-section at 400, having a generally cylindrical housing 402. The flow module is similar to that shown in FIG. 9, having ultrasonic transducers 404 and 406 transmitting and receiving ultrasonic pulses along a path oblique to the main flow path 408. The inside surface of the housing 402, which forms the flow path 408, is lined with pathogen-resistant liner 410. The liner material preferably does not significantly attenuate ultrasound radiation, and the cross-sectional shape of liner is matched that of the flow path. The liner 410 is permeable to molecular gases so that an oxygen sensor 412 and a carbon dioxide sensor 414 are responsive to compositional changes in respiratory gases passing through the flow path. The indentations 416 and 418 are air filled, but in other embodiments may be filled with gel so as to increase ultrasonic coupling between the transducers and the flow path. The sensors and transducers are connected to an interface module 420 using wires such as 422. The interface module is preferably a socket to which an electronics module, cable, or wireless communications module is connected. The pathogen resistant liner element 410 protects the ultrasonic transducers and gas sensors from contamination due to the flow of gas through the tube. The liner can be removed and replaced between patients.

In other embodiments, the liner 410 may be provided with a fluorescent gas sensing element, which may be used in conjunction with an oxygen sensor analysis module and electronic module in a manner similar to those methods described above.

In addition to the functionality described in U.S. application Ser. No. 09/630,398, other respiratory parameters may be calculated, such as peak flow, tidal volume, respiratory frequency, FEV1, and the like. These parameters are useful in monitoring respiratory performance, and diagnosing problems. Further discussion is given in co-pending U.S. provisional application Serial No. 60/236,829 (filed Sep. 29, 2000), which is incorporated by reference. Flow parameters which may be determined have been listed by Acorn in U.S. Pat. No. 5,705,735 (column 7, line 24 through column 8, line 4), which is incorporated herein by reference. Respiratory parameters may be determined using methods described by Daniels et al. in U.S. Pat. No. 6,099,481, incorporated herein by reference. Respiratory parameters, respiratory quotient, resting metabolic rate (or resting energy expenditure), flow-volume curves, and other tabular or graphical data may be shown on a display on the housing of the electronics module. If the functionality of the electronics module is incorporated into other medical equipment, such as a ventilator, intravenous feeding unit control, EKG monitor, oximeter, or the like, then the display of that device can be used. The respiratory analyzer sensors may also provide additional information such as pulmonary function, lung mechanics, work of breathing, FRG, and nitric oxide (inhaled and/or exhaled). This information can be communicated via cable or other means to the mechanical ventilator, whereby ventilator settings can be optimally adjusted to suit the conditions of the lung. Alternatively, the calorimeter could communicate with an enteral or parenteral infusion pump to adjust the nutrition support according to the measured nutritional needs as determined by the calorimeter. This is discussed in more detail below.

Integration of flow and gas concentration data gives the gas volumes inhaled and exhaled. Subtraction of exhaled oxygen volume from inhaled oxygen volume gives the volume of oxygen consumption, $VO_2$. Using a carbon dioxide detector $VCO_2$ can also be determined. This parameter may also be determined without using the carbon dioxide detector, for example by assuming a respiratory quotient.

If the diet of a person is known, for example using an electronic diet log, or by administrating a controlled food composition to a patient, the respiratory quotient may be calculated from the nutrients that the person is expected to be consuming at the time of measurement. A model of a person's physiology can be developed so as to allow calculation of respiratory quotient based on the time and nature of meals eaten.

The metabolic rate of the person can be found using the Weir equation, as described in U.S. Pat. No. 5,705,735 to Acorn, and U.S. Pat. Nos. 6,135,107 and 5,836,300 to Mault, incorporated herein by reference. Nitrogen metabolism levels can be determined from analysis of urine, or since this factor is relatively small, an estimated value may be used. The determined resting metabolic rate can be used to control the feeding of a patient. If a patient is consuming a nutritionally balanced food composition, the amount of food which needs to be administered can be determined using the metabolic rate. If a patient is being fed intravenously, an infusion pump can be controlled by the electronics module. The infusion pump preferably comprises an electronic controller responsive to metabolic rate data provided by an indirect calorimeter.

In another embodiment, the infusion pump has an electronic control system that comprises the functionality of the electronics module. The control system contains an electronic circuit to analyze the signals from the sensors and/or transducers of the flow module, calculate a metabolic rate for the patient on the ventilator, and control the rate of the infusion pump motor as a function of metabolic rate.

Figure 15:
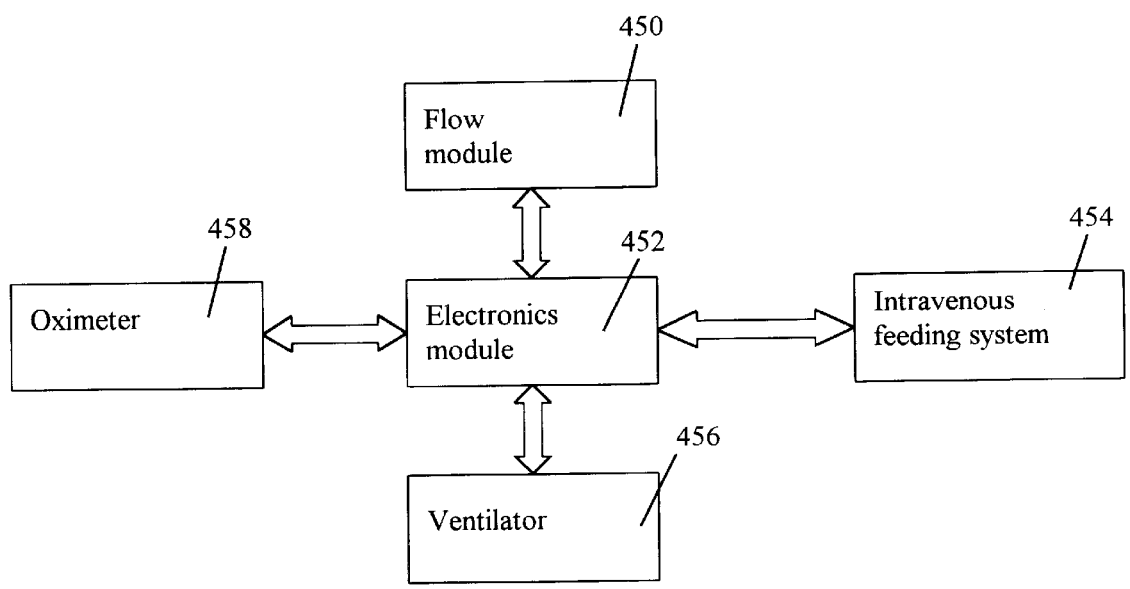
FIGS. 15 and 16 illustrate a system embodiment with automatic control of patient feeding.

FIG. 15 shows a system in which sensor data from flow module 450 is analyzed by electronics module 452, and the determined metabolic rate used to control an intravenous feeding system 454. The electronics module also receives data from an oximeter, which determines the oxygen content of the patient's blood. This may be placed on a finger of the patient and wired to the electronics module. Blood oxygenation and carbon dioxide content can be determined from end tidal oxygen and carbon dioxide content for exhaled gas. Data is sent to the ventilator to control the oxygen supply to the patient.

Figure 16:
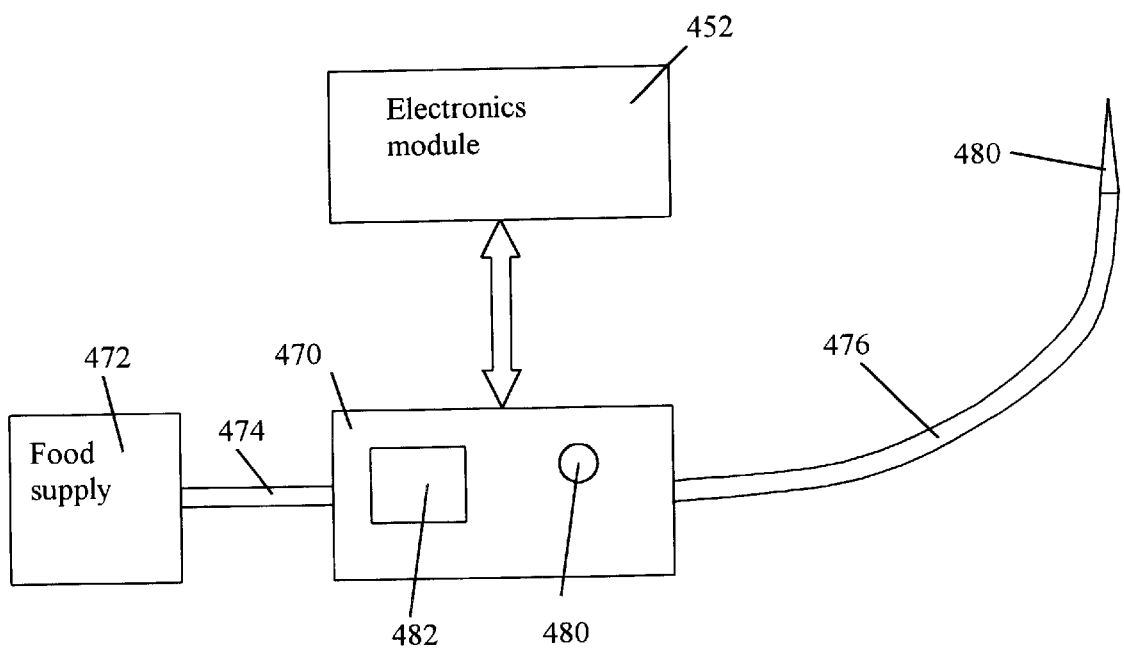

FIG. 16 shows a possible intravenous feeding system which can be used with the present invention. A nutritional pump 470 draws a nutritional fluid (liquid food) from food supply device 472 along food supply pipe 474. Based on data received from the electronics module (452 in FIG. 15) concerning the metabolic rate of the patient, the nutritional pump (or infusion pump) 470 supplies nutritional fluid to the patient along feeding tube 478 and through feeding needle 480. The needle may be inserted under the skin of the patient into a vein. The pump 470 preferably has a preferred range of operation and cannot be operated outside this range without medical intervention. A display 482 is provided on the housing of the pump to show the rate of intravenous administration of nutrition, and possibly the metabolic rate of the person as determined by the improved respiratory analyzer. An alarm 480 sounds and flashes if the patients metabolic rate is outside of a predetermined range.

Figure 17:
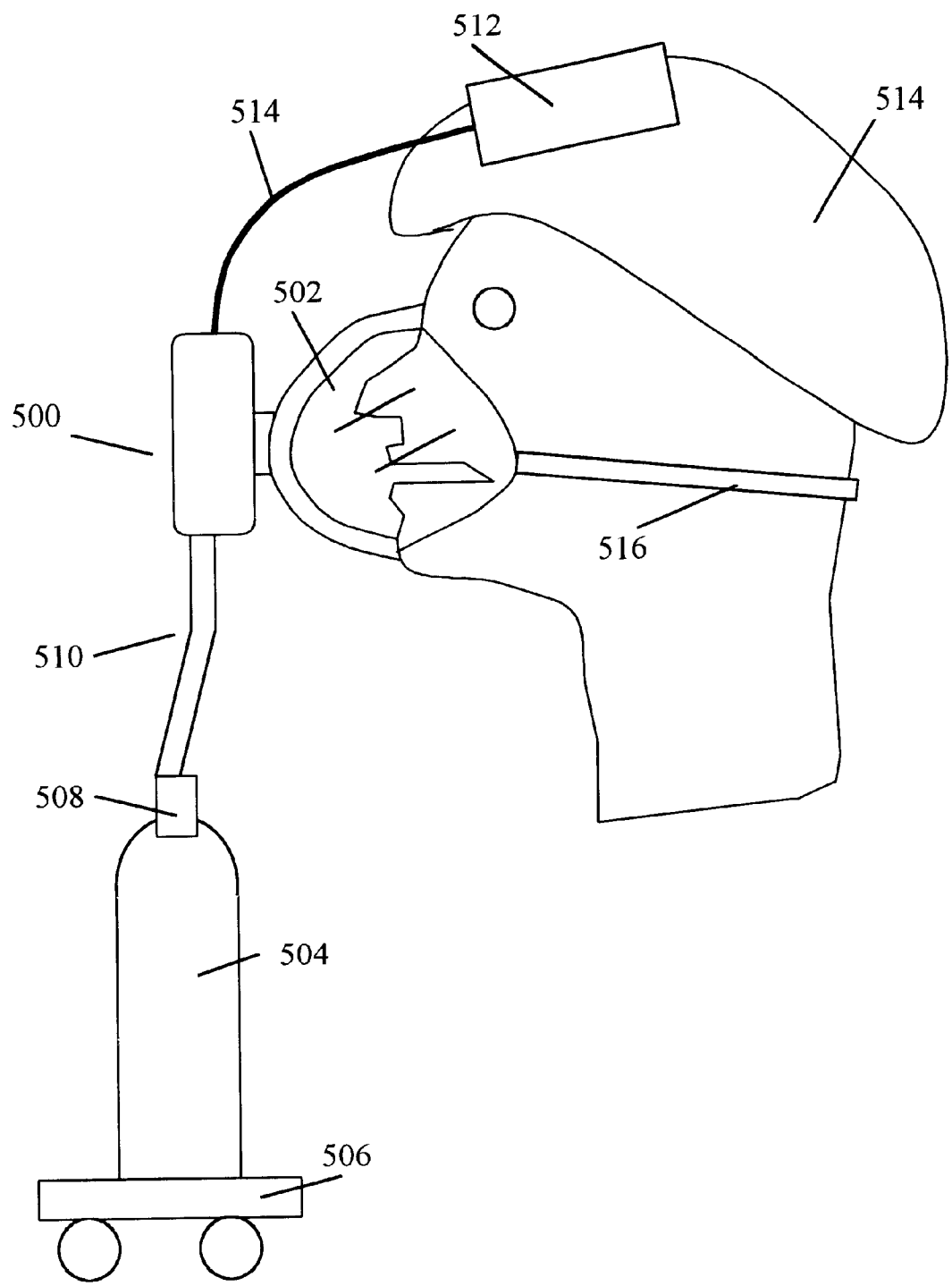
FIG. 17 shows a respiratory analyzer system with a helmet mounted electronics module.

The metabolism of a patient, or other person, walking around or otherwise mobile, can be monitored using a helmet based calorimeter system. FIG. 17 shows a person breathing through face mask 502. A flow module 500 is in fluid communication with the face mask. Oxygen is provided by cylinder 504, mounted on trolley 506. Oxygen pressure is controlled by regulator 508, and oxygen then passes along tube 510 to flow module 500. The flow module is linked by cable 514 to an electronics module contained within helmet 512. In another preferred embodiment the flow tube is in wireless communication with the electronics module, so that cable 514 is not required. An electronics module may also clip on to a helmet. Exhaled air is vented to the atmosphere, preferably after passing through the flow module. A valve system can be used to control the flow of in inhaled and exhaled gases, so as to direct exhaled gases to the atmosphere. The mouthpiece can be supported by the helmet, or by elastic straps around the head of the person.

The helmet based system can be used with other ventilator systems, or with a gas cylinder carried in a backpack, e.g. for high altitude breathing assistance for healthy individuals. The helmet based system can also be used to determine the metabolic rate of a person breathing air. Advantages include the removal of heat-generating electronics from the sensors and transducers, and reduction of the weight of the flow module supported by the mask or a mouthpiece.

Figure 18:
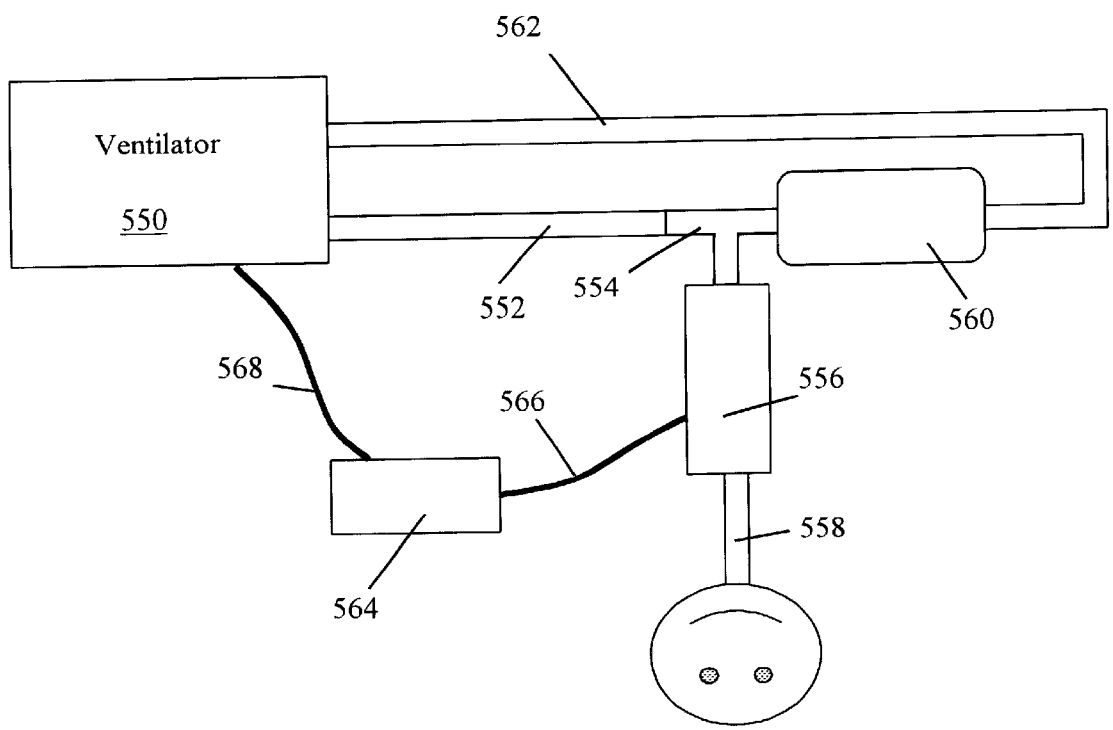
FIG. 18 shows a system for determination of cardiac output.

The improved respiratory analyzer of the present invention can be used to determine cardiac output. FIG. 18 shows a modified ventilator system having a reservoir for exhaled gas. The modified system comprises a ventilator 550, a inlet tube 552, a valve unit 554, a flow module 556, a patient intubation device 558, an exhaled gas reservoir 560, a return tube 562, and an electronics module 564, which is connected to the flow module by cable 566 and to the ventilator by cable 568. In normal breathing, the valve 554 allows only gases supplied by the ventilator to the patient. During exhalation, exhaled gas passes out through the valve 554 into the reservoir 560 and return tube 562. The cardiac output of the patient can be determined by the method described by Mault in U.S. Pat. No. 6,135,107, incorporated herein by reference. The valve unit 554 is reconfigured so as to allow exhaled air stored in reservoir 560 to be re-breathed by the patient. The flow module comprises a flow path, a pair of ultrasonic transducers disposed so as to measure flow rates through the flow path, and a capnometer (carbon dioxide sensor). The flow module provides a signal to the electronics module, containing data correlated with flow rate and carbon dioxide concentration in the respired gases. The change in arterial carbon dioxide (carbonate) due to the partial rebreathing of exhaled carbon dioxide is monitored using the end tidal carbon dioxide level of exhaled breath. Flow rate data is integrated with carbon dioxide concentration data, using a processor in the electronics module, so as to determine total inhaled and exhaled carbon dioxide volumes and the concentration of carbon dioxide at the end of an exhalation (the end tidal concentration). These values are converted to cardiac output using an algorithm running on the electronics module based on the method of U.S. Pat. No. 6,135,107, in which cardiac output is determined from change in carbon dioxide production divided by change in end-tidal carbon dioxide concentration. Valve 554 is returned to the normal configuration after the end of the test, which may take approximately 30 seconds.

The gas stored in the reservoir 560 can also be analyzed for trace components, such as nitric oxide and metabolic disorder indicators, using techniques such as spectroscopy which benefit from larger gas volumes.

If a patient is intubated, the flow module is preferably located near the point of intubation. If the patient is not intubated, a mouthpiece or mask is provided, or the flow module can be shaped so as to be placed in the patients mouth. A general cylindrical shape is suitable to be placed in the mouth.

The separation of the respiratory analyzer into a flow module and an electronics module allows placing the flow module into the patient's trachea, reducing dead space and increasing the accuracy of the measurements. In this embodiment, the flow module is preferably cylindrical, having a pair of micromachined ultrasonic transducers disposed to determine flow rates through the flow path. If the person's ventilatory equivalent is determined, then the oxygen consumption and metabolic rate of the person can be determined from flow rates alone. Alternatively, oxygen consumption can be determined from flow rates and gas density determination using ultrasound transducers, as described in Int. Pat. App. No. WO00/7498 to Mault, incorporated herein by reference.

Figure 19:
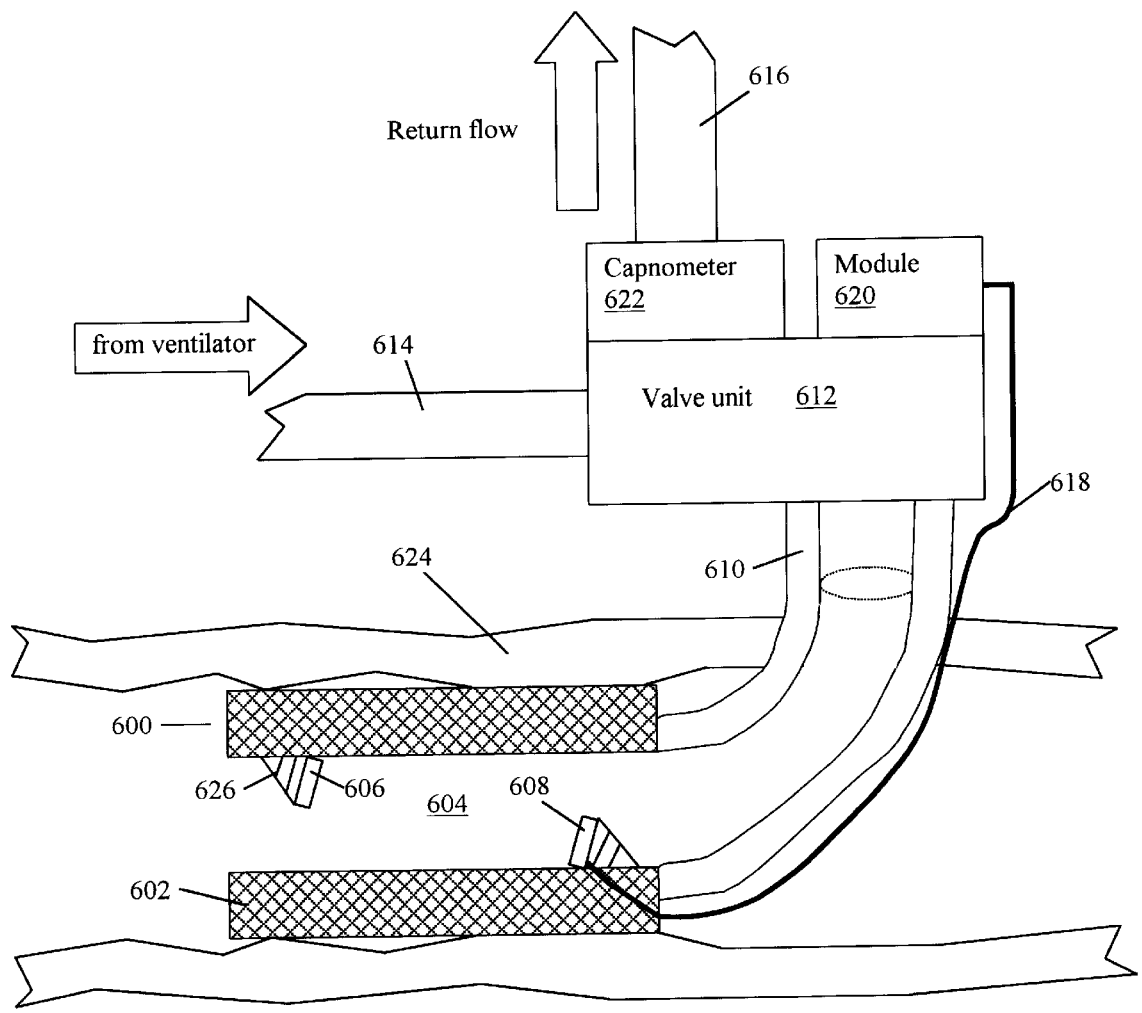
FIG. 19 shows a tracheal flow module.

FIG. 19 shows a flow module 600 installed in the trachea of a patient, having a generally cylindrical housing 602, enclosing a flow path 604, and a pair of ultrasonic transducers 606 and 608 disposed to transmit and receive ultrasonic pulses along a direction having a direction component along the flow path. A flexible tube 610 exits the patient's trachea through a hole (or through the mouth), and connects to a valve unit 612. Gas from the ventilator arrives along inhalation conduit 614, and exhaled gas passes along exhalation conduit 616. A cable 618 connects the transducers in the flow module to suitable drive and analysis circuitry in the electronics module 620. Preferably, the ultrasonic transducers are micromachined devices adapted to operate at non-hazardous voltages. A capnometer 622 in the exhalation conduit provides an independent measurement of carbon dioxide exhalation volume. Element 626 is a transducer support.

In other embodiments, ultrasonic analysis of gas flow within the body is achieved by electromagnetic excitation of transducers within the body using a radiation source outside of the body. For example, an inductor in the flow module is used to provide electrical power to a transducer, and is powered by an external radiation source. The tracheal module can also be pushed down through the mouth of a breathing subject, so that the flexible tube and wire emerge from the mouth. The flow module and electronics module may also communicate using a wireless communications link.

Figure 20:
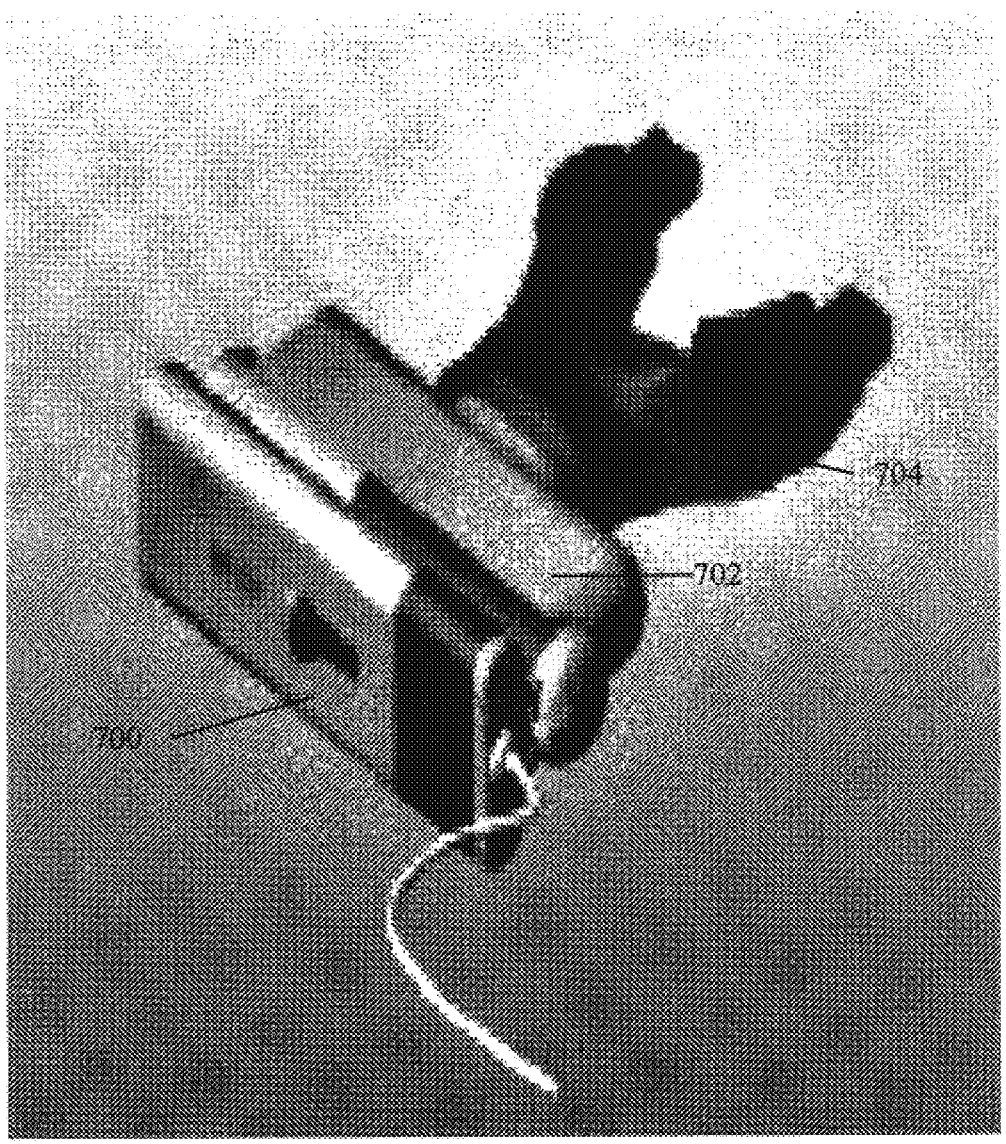
FIGS. 20 and 21 show designs for other embodiments using an electronics module.
Figure 21:
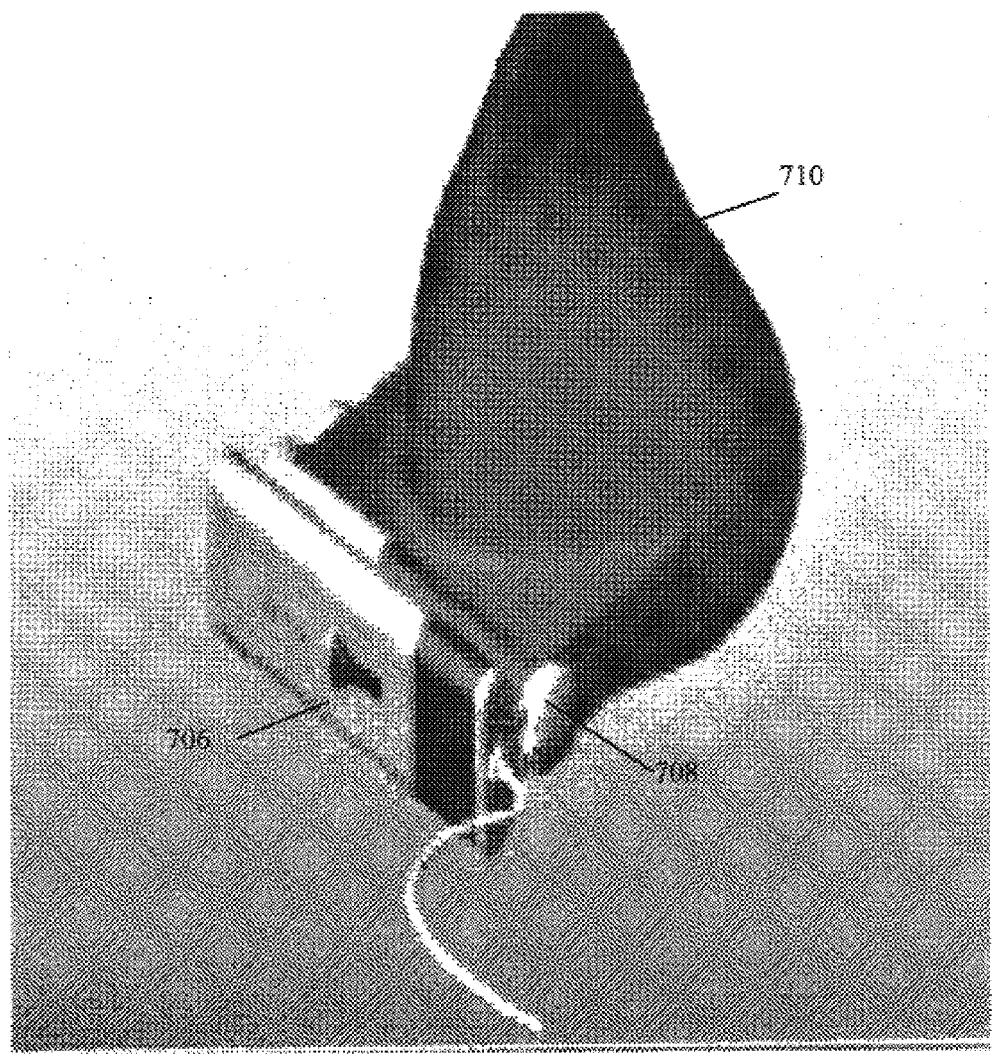

FIGS. 20 and 21 show embodiments in which an electronics module 700 may be used in various form factors of flow module and flow path. In FIG. 20, electronics module 700 forms an interface with a flow module 702 in fluid connection with a mouthpiece 704. This configuration is an alternative embodiment of the gas exchange monitor (GEM). FIG. 21 shows electronics module 706 forming an electrical and mechanical interface with flow module 708 which is then in connection with face mask 710.

We have described embodiments of an indirect calorimeter for use with a mechanical ventilator apparatus in which the disposable flow tube is adapted to be removably inserted in the ventilator line connecting the mouthpiece or endotracheal tube with the forced ventilator apparatus. The non-disposable section of the calorimeter, incorporating the flow meter and gas sensor apparatus and associated electronics, may be physically attached to the forced ventilator apparatus so as to be engaged with the disposable section when it is inserted into the ventilator line, or, alternatively, may be supported on the disposable section which is in turn supported by the ventilator apparatus. The disposable section may incorporate a fluorescent coating forming part of a fluorescence oxygen quench sensor.

Other embodiments of the invention will be clear to those skilled in the art. The examples and embodiments given are not limiting. The invention is defined by the following claims.

We claim:

1. A ventilator system for assisting a patient in breathing comprising:
    a supply of inhalation respiratory gases;
    a respiratory conduit providing a flow pathway for an inhalation and exhalation respiratory gas flowing therethrough between said supply of inhalation respiratory gases and the patient;
    a valve disposed within said respiratory conduit for controlling the flow of inhalation and exhalation respiratory gases;
    a flow module holder located within the conduit between said valve and the patient; and
    a respiratory gas analyzer located between said valve and the patient, the analyzer comprising:
        a flow module, adapted to be placed within the flow module holder in the conduit, so that the inhalation and exhalation respiratory gases pass through a flow path of the flow module, the flow module containing a flow rate sensor disposed in the flow path of the flow module for determining a flow rate of the inhalation and exhalation respiratory gases, and
        an electronics module, adapted to be integrally connected to the flow module, and adapted to calculate a respiratory parameter using the determined flow rate of the inhalation and exhalation respiratory gases flowing through the flow path.

2. The ventilator system of claim 1, wherein the supply of respiratory gas is a mechanical ventilator.

3. The ventilator system of claim 1, wherein the flow sensor comprises a pair of ultrasonic transducers operable so as to provide a signal correlated with flow rate through the flow path.

4. The ventilator system of claim 1 wherein the flow module includes a generally cylindrical housing, an ultrasonic transducer transmitting and receiving ultrasonic pulses along a path oblique to the flow of inhalation and exhalation respiratory gas in the flow path, a pathogen-resistant liner lining an inside surface of the housing to protect the ultrasonic transducer and a gas component concentration sensor disposed in the flow path from contamination due to the flow of inhalation and exhalation respiratory gas, wherein the liner is replaceable.

5. The ventilator system of claim 1, wherein the electronics module is adapted to calculate a metabolic rate of the patient.

6. The ventilator system of claim 1 wherein the flow module is disposable and the electronics module is non-disposable, and the flow module is removably mounted to the electronics module.

7. The ventilator system of claim 1 wherein the flow module includes a housing enclosing the flow path, and the flow sensor is mounted in the flow path on the housing.

8. A ventilator system adapted to be placed in fluid communication with an airway of a patient comprising:
    a supply of inhalation respiratory gas;
    a respiratory conduit providing a flow pathway for an inhalation and exhalation respiratory gas flowing therethrough;
    an inlet conduit operatively connected between the supply of respiratory gas and the respiratory conduit for directing an inhalation respiratory gas to the patient;
    a return conduit operatively connected between the supply of inhalation respiratory gas and the ventilator, for returning exhalation respiratory gas to the supply of respiratory gas;
    a valve disposed between the inlet conduit, respiratory conduit and outlet conduit for controlling the flow of gas to each of the conduits;
    a respiratory gas analyzer operatively positioned in the patient's airway, wherein the respiratory gas analyzer includes a disposable flow module having a flow path operatively connected to a non-disposable electronics module;
    an ultrasonic flow sensor in fluid communication with the flow path for detecting gas flow volume in the flow path; and
    a gas component sensor in fluid communication with the flow path for detecting gas component concentration levels in the flow path, wherein the electronics module uses the gas flow volume and gas component concentration level to determine a metabolic rate of the patient.

9. The ventilator system of claim 8 wherein the flow module is operatively connected to the electronics module using a wireless communications link.

10. The ventilator system of claim 8 wherein the flow module is operatively connected to the electronics module using a wired communications link.

11. The ventilator system of claim 8 wherein the flow module includes a housing enclosing the flow path, and the flow sensor is mounted in the flow path on the housing.

12. The ventilator system of claim 8 wherein the gas component sensor is an oxygen sensor in fluid communication with the flow path for determining an oxygen concentration level of the respiratory gas flowing through the flow path.

13. The ventilator system of claim 8 wherein the gas component sensor is a carbon dioxide sensor in fluid communication with the flow path for determining the level of carbon dioxide of the respiratory gas flowing through the flow path.

14. The ventilator system of claim 8 wherein the electronics module includes a housing, a circuit board disposed within the housing, a transducer interface and a transducer connector for communicating with the flow sensor and the gas component sensor, a processor, memory and a display.

15. The ventilator system of claim 8 wherein generally cylindrical housing, ultrasonic transducers transmitting and receiving ultrasonic pulses along a path oblique to the flow of respiratory gas in the flow path, a pathogen-resistant liner lining an inside surface of the housing to protect the ultrasonic transducer and gas component concentration sensor from contamination due to the flow of respiratory gas, wherein the liner is replaceable.

16. A system for providing intravenous feeding to a person connected to a ventilator, the method comprising:
    a ventilator system, having a holder adapted to receive a flow module;
    an indirect calorimeter, comprising a non-disposable electronics module and a disposable flow module, the flow module enclosing a flow path, the flow module being placed within the holder of the ventilator system so that gases respired by the person pass through the flow path;
    an intravenous feeding unit, the unit comprising a source of intravenous food, a delivery tube for delivering the food to the person, and a pump adapted to pump intravenous food from the source along the delivery tube at a controlled pump rate; and a communications link between the indirect calorimeter and the infusion pump, so as to modify the controlled pump rate of food to the person according to data provided by the indirect calorimeter.

17. A ventilator system adapted to be placed in fluid communication with an airway of a patient comprising:

a supply of inhalation respiratory gases;

a respiratory conduit providing a flow pathway for an inhalation and exhalation respiratory gas flowing therethrough;

a flow module holder located within the conduit; and a respiratory gas analyzer, the analyzer comprising:

a flow module, adapted to be placed within the flow module holder in the conduit, so that the inhalation and exhalation respiratory gases pass through a flow path of the flow module, the flow module containing a flow rate sensor for determining a flow rate of the inhalation and exhalation respiratory gases, wherein the flow module is disposed in the airway of the patient and includes a generally cylindrical housing enclosing the flow path, a pair of ultrasonic transducers positioned to transmit and receive ultrasonic pulses along a direction having a direction component along the flow path, a flexible tube disposed between the flow module and a valve unit, and a capnometer in the exhalation conduit for measuring a volume of carbon dioxide in the exhaled respiratory gas, and an electronics module, adapted to be connected to the flow module, and adapted to calculate a respiratory parameter using the determined flow rate of the inhalation and exhalation respiratory gases flowing through the flow path.

18. A ventilator system for assisting a patient in breathing comprising:

a supply of inhalation respiratory gases;

a respiratory conduit providing a flow pathway for an inhalation and exhalation respiratory gas flowing therethrough between said supply of inhalation respiratory gases and the patient;

a valve disposed within said respiratory conduit for controlling the flow of inhalation and exhalation respiratory gases;

a flow module holder located within the conduit between said valve and the patient;

a gas component sensor, sensitive to a respiratory gas component, operable so as to provide a signal correlated with an instantaneous concentration of a respiratory gas component; and a respiratory gas analyzer located between said valve and the patient, the analyzer comprising:

a flow module, adapted to be placed within the flow module holder in the conduit, so that the inhalation and exhalation respiratory gases pass through a flow path of the flow module, the flow module containing a flow rate sensor disposed in the flow path of the flow module for determining a flow rate of the inhalation and exhalation respiratory gases, and an electronics module, adapted to be integrally connected to the flow module, and adapted to calculate a respiratory parameter using the determined flow rate of the inhalation and exhalation respiratory gases flowing through the flow path.

19. The ventilator system of claim 18 further comprising a gas component sensor, wherein the gas component sensor is an oxygen sensor analysis module having a housing, an electronics circuit, an excitation radiation source, a sensing channel optical detector, a reference channel optical detector and external connection, such that the oxygen sensor analysis module is disposed within an indentation of a housing for the flow module having a sensing channel fluorescent film and reference channel fluorescent film on its inner surface, and the surface of the sensing channel film is exposed to the inhalation and exhalation respiratory gas flow and the reference channel film is protected from the oxygen in the inhalation and exhalation respiratory gas flow by an oxygen-impermeable film, and a transparent wave guide film for optical coupling between the oxygen sensor analysis module and the fluorescent film, for measuring oxygen consumption by the patient.

20. The ventilator system of claim 18 further comprising a gas component sensor disposed in the flow module, wherein the gas component concentration sensor measures the concentration of nitric oxide in the inhaled respiratory gas.

21. The ventilator system of claim 18 further comprising a gas component sensor disposed in the flow module, wherein the gas component concentration sensor measures the concentration of gas components in the exhaled respiratory gas.

22. The ventilator system of claim 18 further comprising a gas component sensor disposed in the flow module, wherein the gas component sensor is an oxygen sensor in fluid communication with the flow path for determining an oxygen concentration level of the inhalation and exhalation respiratory gas flowing through the flow path.

23. The ventilator system of claim 18 further comprising a gas component sensor disposed in the flow module, wherein the gas component sensor is a carbon dioxide sensor in fluid communication with the flow path for determining a level of carbon dioxide of the inhalation and exhalation respiratory gas flowing through the flow path.

24. The ventilator system of claim 18 wherein the flow module holder is a connecting means.

25. The ventilator system of claim 24 wherein the connecting means is a connector and a collar.

26. The ventilator system of claim 18 wherein the flow module includes an inlet portion connected to a first lateral offset portion, that is connected to a central portion, that is connected to a second lateral offset portion, and also connected to an outlet portion.

27. The ventilator system of claim 18 wherein the electronics module includes a housing, a circuit board disposed within the housing, a transducer interface and a transducer connector for communicating with the flow sensor, a processor, a memory and a display.

28. The ventilator system of claim 27 wherein the electronics module includes a micromachined ultrasonic transducer containing an array of micromachined temperature, pressure and humidity sensing elements.

29. The ventilator system of claim 18 wherein the flow sensor and the gas component sensor are disposed in the flow path of the flow module, and the flow module is connected to the electronics module using a wireless communications link.

30. The ventilator system of claim 18 wherein the flow module includes a housing enclosing the flow path formed by a first chamber, a central flow path and a second chamber, such that the first chamber and second chamber are separated by a partition to provide a coaxial flow geometry of the respiratory gas.

31. The ventilator system of claim 18 wherein the flow module includes a housing enclosing the flow path formed by a first chamber, a central flow path formed by a circular flow tube, a second chamber, and a partition separating the first and second chambers, such that a direction of the inhalation and exhalation respiratory gas flow in the central flow path is perpendicular to a flow direction of inhaled respiratory gas.

32. The ventilator system of claim 18 wherein the flow module includes a housing enclosing a ventilator-side chamber, a central flow path formed by a flow tube, a patient-side chamber, and a partition separating the ventilator-side and patient-side chambers.

33. The ventilator system of claim 18 wherein the flow module includes a housing surrounding a central flow path, a recess formed within an inside surface of the housing for supporting an ultrasonic transducer within the flow path, an oxygen sensor positioned to sense the inhalation and exhalation respiratory gas flow along the central flow path, and an interface unit for transferring a signal between the ultrasonic transducer, and oxygen sensor and electronics module.

34. The ventilator system of claim 18 wherein the flow module includes a housing having a generally cylindrical shape surrounding a flow path, a strut within the housing for supporting an ultrasonic transducer within the flow path, an oxygen sensor positioned to sense the respiratory gas flow along the flow path, and an interface unit for transferring a signal between the ultrasonic transducer, and oxygen sensor and electronics module.

35. The ventilator system of claim 18 wherein the flow module includes a housing having a generally cylindrical shape surrounding a central flow path, an ultrasonic transducer within the flow path, an indentation in a top surface of the housing for receiving an external oxygen sensor that is removable from the flow module, and an interface unit for transferring a signal between the ultrasonic transducers, oxygen sensor and electronics module.

36. The ventilator system of claim 18 wherein the flow module includes a housing having an oxygen sensitive fluorescent coating on an inner surface of the housing, a transparent membrane separating the fluorescent coating from an external radiation source and detector, wherein an optical fiber conveys excitation radiation to the fluorescent coating and fluorescent radiation from the fluorescent coating returns along the optical fiber.

* * * * *